(12) United States Patent
Camps et al.

(10) Patent No.: US 12,311,200 B2
(45) Date of Patent: May 27, 2025

(54) MULTIPLANAR MOTION MANAGEMENT SYSTEM

(71) Applicant: EBAMed SA, Geneva (CH)

(72) Inventors: Saskia Camps, Prangins (CH); Jérémie Gringet, Lausanne (CH); Rosalind Perrin, Satigny (CH); Adriano Garonna, Geneva (CH)

(73) Assignee: EBAMed SA, Geneva (CH)

( * ) Notice: Subject to any disclaimer, the term of this patent is extended or adjusted under 35 U.S.C. 154(b) by 0 days.

(21) Appl. No.: 18/597,839

(22) Filed: Mar. 6, 2024

(65) Prior Publication Data
US 2024/0261596 A1    Aug. 8, 2024

Related U.S. Application Data

(63) Continuation of application No. 18/269,351, filed as application No. PCT/IB2021/000922 on Dec. 23, 2021.

(Continued)

(51) Int. Cl.
*A61N 5/10* (2006.01)
*A61B 5/33* (2021.01)

(52) U.S. Cl.
CPC .............. *A61N 5/1068* (2013.01); *A61B 5/33* (2021.01); *A61N 2005/1058* (2013.01)

(58) Field of Classification Search
None
See application file for complete search history.

(56) References Cited

U.S. PATENT DOCUMENTS 3,399,302 A    8/1968   Carrell
3,923,060 A   12/1975   Ellinwood, Jr.
(Continued)

FOREIGN PATENT DOCUMENTS

BE    1024702 A1     5/2018
CA    2781536 A1    12/2012
(Continued)

OTHER PUBLICATIONS

Achenbach S., et al., "Noninvasive Coronary Angiography by Retrospectively ECG-Gated Multislice Spiral CT," Circulation, 102(23):2823-2828 (Dec. 2000).
(Continued)

*Primary Examiner* — Carrie R Dorna
*Assistant Examiner* — Marc D. Honrath
(74) *Attorney, Agent, or Firm* — Greenberg Traurig, LLP; Christopher C. Bolten; Robert D. Ward

(57) ABSTRACT

A multiplanar motion management system to aid in administering non-invasive radiation therapies. The disclosed devices and techniques enable clinicians to accurately monitor the position and motion of the heart with respect to a reference situation of the simulation stage. In addition, information is provided about the respiratory phase of the patient as well as about possible drifts of the anatomical structures. This information can be used by the clinician to interrupt the radiation treatment manually when necessary. The information can also be used to automatically, and in real-time, provide the appropriate gating signals to the therapy machine. The disclosed system may be configured to cover all motion aspects required during a typical radiotherapy workflow with just one device, from patient setup (inter-fraction motion monitoring) to cardiac and respiratory motion monitoring during the treatment (intra-fraction motion monitoring).

8 Claims, 5 Drawing Sheets

Related U.S. Application Data

(60) Provisional application No. 63/129,694, filed on Dec. 23, 2020.

(56) References Cited

U.S. PATENT DOCUMENTS

| | | | |
|---|---|---|---|
| 5,411,026 A * | 5/1995 | Carol | A61B 8/08 128/916 |
| 5,538,494 A | 7/1996 | Matsuda | |
| 5,590,657 A | 1/1997 | Cain et al. | |
| 5,718,241 A | 2/1998 | Ben-Haim et al. | |
| 5,764,723 A | 6/1998 | Weinberger et al. | |
| 5,909,476 A | 6/1999 | Cheng et al. | |
| 6,144,875 A | 11/2000 | Schweikard et al. | |
| 6,443,896 B1 | 9/2002 | Detmer | |
| 6,658,285 B2 | 12/2003 | Potse et al. | |
| 6,710,362 B2 | 3/2004 | Kraft et al. | |
| 6,780,152 B2 | 8/2004 | Üstüner et al. | |
| 6,863,653 B1 | 3/2005 | Zanelli et al. | |
| 6,889,695 B2 | 5/2005 | Pankratov et al. | |
| 7,260,426 B2 | 8/2007 | Schweikard et al. | |
| 7,322,929 B2 | 1/2008 | Lovoi | |
| 7,346,381 B2 | 3/2008 | Okerlund et al. | |
| 7,565,190 B2 | 7/2009 | Okerlund et al. | |
| 7,645,276 B2 | 1/2010 | Pankratov et al. | |
| 7,853,313 B2 | 12/2010 | Thomson | |
| 7,953,204 B2 | 5/2011 | Sumanaweera et al. | |
| 8,278,633 B2 | 10/2012 | Nord et al. | |
| 8,295,435 B2 | 10/2012 | Wang et al. | |
| 8,295,906 B2 | 10/2012 | Saunders et al. | |
| 8,348,846 B2 * | 1/2013 | Gunther | A61B 8/4245 600/443 |
| 8,351,571 B2 | 1/2013 | Brinks et al. | |
| 8,422,631 B2 | 4/2013 | Takahashi et al. | |
| 8,488,910 B2 | 7/2013 | Ruijters | |
| 8,784,290 B2 | 7/2014 | Sumanaweera et al. | |
| 8,792,613 B2 | 7/2014 | Gardner et al. | |
| 8,805,481 B2 | 8/2014 | Sumanaweera et al. | |
| 8,824,757 B2 | 9/2014 | Kolthammer et al. | |
| 9,014,424 B2 | 4/2015 | Berlinger et al. | |
| 9,061,144 B2 | 6/2015 | Fujii et al. | |
| 9,108,048 B2 | 8/2015 | Maurer, Jr. et al. | |
| 9,205,279 B2 | 12/2015 | Sumanaweera et al. | |
| 9,289,268 B2 | 3/2016 | Ramraj et al. | |
| 9,320,916 B2 | 4/2016 | Sumanaweera et al. | |
| 9,326,751 B2 | 5/2016 | Hastings | |
| 9,504,853 B2 | 11/2016 | Sumanaweera et al. | |
| 9,526,476 B2 | 12/2016 | Schwartz et al. | |
| 9,750,957 B2 | 9/2017 | Fujii et al. | |
| 9,789,339 B2 | 10/2017 | Moskvin et al. | |
| 9,907,978 B2 | 3/2018 | Pankratov et al. | |
| 9,962,562 B2 | 5/2018 | Fahrig et al. | |
| 9,968,801 B2 | 5/2018 | Sumanaweera et al. | |
| 10,029,121 B2 | 7/2018 | Li et al. | |
| 10,159,446 B2 | 12/2018 | Dickerson | |
| 10,166,406 B2 | 1/2019 | Nord et al. | |
| 10,251,629 B2 | 4/2019 | Belt et al. | |
| 10,265,543 B2 | 4/2019 | Bharat et al. | |
| 10,286,228 B2 | 5/2019 | Bharat et al. | |
| 10,315,049 B2 | 6/2019 | Gauthier et al. | |
| 10,342,558 B2 | 7/2019 | Steckner et al. | |
| 10,363,439 B2 | 7/2019 | Amaldi | |
| 10,485,992 B2 | 11/2019 | Heese et al. | |
| 10,500,418 B2 | 12/2019 | Filiberti et al. | |
| 10,548,496 B2 | 2/2020 | Gijsbers et al. | |
| 10,646,188 B2 | 5/2020 | Mostafavi et al. | |
| 10,792,511 B2 | 10/2020 | Pankratov et al. | |
| 10,974,069 B2 | 4/2021 | Maguire et al. | |
| 11,097,127 B2 | 8/2021 | Sumanaweera et al. | |
| 11,272,902 B2 | 3/2022 | Geelen et al. | |
| 11,298,565 B2 | 4/2022 | Garonna et al. | |
| 11,406,845 B2 | 8/2022 | Robinson et al. | |
| 11,506,801 B2 | 11/2022 | Sauli et al. | |
| 11,857,808 B2 | 1/2024 | Packer et al. | |
| 11,951,327 B2 | 4/2024 | Garonna et al. | |
| 2002/0072674 A1 | 6/2002 | Criton et al. | |
| 2002/0095197 A1 | 7/2002 | Lardo et al. | |
| 2004/0015075 A1 | 1/2004 | Kimchy et al. | |
| 2004/0162596 A1 | 8/2004 | Altshuler et al. | |
| 2004/0260142 A1 | 12/2004 | Lovoi | |
| 2004/0267113 A1 | 12/2004 | Thomson | |
| 2005/0171396 A1 | 8/2005 | Pankratov et al. | |
| 2006/0039591 A1 | 2/2006 | Zettel et al. | |
| 2006/0074292 A1 | 4/2006 | Thomson et al. | |
| 2006/0215819 A1 * | 9/2006 | Moyers | A61B 6/0487 378/205 |
| 2006/0224053 A1 | 10/2006 | Black et al. | |
| 2006/0241443 A1 | 10/2006 | Whitmore et al. | |
| 2006/0285641 A1 * | 12/2006 | Scherch | A61N 5/1049 378/65 |
| 2006/0291621 A1 | 12/2006 | Yan et al. | |
| 2007/0041499 A1 | 2/2007 | Lu et al. | |
| 2008/0021300 A1 | 1/2008 | Allison | |
| 2008/0023644 A1 | 1/2008 | Pedroni | |
| 2008/0081982 A1 | 4/2008 | Simon et al. | |
| 2008/0177279 A1 * | 7/2008 | Sumanaweera | A61N 5/1068 901/41 |
| 2008/0177280 A1 | 7/2008 | Adler et al. | |
| 2008/0191142 A1 | 8/2008 | Pedroni | |
| 2008/0221382 A1 | 9/2008 | Karshafian et al. | |
| 2008/0317204 A1 | 12/2008 | Sumanaweera et al. | |
| 2009/0074278 A1 | 3/2009 | Beaulieu et al. | |
| 2009/0076373 A1 | 3/2009 | Maschke | |
| 2009/0080610 A1 | 3/2009 | Sumanaweera et al. | |
| 2009/0102612 A1 * | 4/2009 | Dalbow | G16H 10/60 340/10.4 |
| 2009/0180589 A1 | 7/2009 | Wang et al. | |
| 2009/0206269 A1 | 8/2009 | Kraft et al. | |
| 2009/0234237 A1 | 9/2009 | Ross et al. | |
| 2009/0238404 A1 | 9/2009 | Orderud et al. | |
| 2009/0253102 A1 | 10/2009 | Porikli et al. | |
| 2009/0257557 A1 | 10/2009 | Sumanaweera et al. | |
| 2009/0306515 A1 | 12/2009 | Matsumura et al. | |
| 2010/0016744 A1 | 1/2010 | Brost et al. | |
| 2010/0016765 A1 | 1/2010 | Hall et al. | |
| 2010/0137709 A1 | 6/2010 | Gardner et al. | |
| 2010/0145358 A1 | 6/2010 | Maschke | |
| 2010/0183120 A1 | 7/2010 | Nord et al. | |
| 2010/0217139 A1 | 8/2010 | Pinter et al. | |
| 2010/0239066 A1 | 9/2010 | Fahrig et al. | |
| 2010/0266099 A1 | 10/2010 | Busch et al. | |
| 2010/0282983 A1 | 11/2010 | Wright et al. | |
| 2010/0301235 A1 | 12/2010 | Bert et al. | |
| 2010/0317968 A1 | 12/2010 | Wright et al. | |
| 2011/0038516 A1 | 2/2011 | Koehler et al. | |
| 2011/0107270 A1 | 5/2011 | Wang et al. | |
| 2011/0137158 A1 | 6/2011 | Sumanaweera et al. | |
| 2011/0160566 A1 | 6/2011 | Petropoulos et al. | |
| 2011/0166407 A1 | 7/2011 | Sumanaweera et al. | |
| 2011/0166408 A1 | 7/2011 | Sumanaweera et al. | |
| 2011/0172526 A1 * | 7/2011 | Lachaine | A61B 8/483 600/443 |
| 2011/0185503 A1 | 8/2011 | Yan | |
| 2011/0190629 A1 | 8/2011 | Guenther et al. | |
| 2011/0218438 A1 | 9/2011 | Hsieh et al. | |
| 2012/0004518 A1 | 1/2012 | D'Souza et al. | |
| 2012/0014501 A1 | 1/2012 | Pelc et al. | |
| 2012/0083645 A1 | 4/2012 | Sun et al. | |
| 2012/0134233 A1 | 5/2012 | Lin et al. | |
| 2012/0146641 A1 | 6/2012 | Wu et al. | |
| 2012/0181428 A1 | 7/2012 | Bert et al. | |
| 2012/0241635 A1 | 9/2012 | Luechtenborg et al. | |
| 2012/0292534 A1 | 11/2012 | Geneser et al. | |
| 2012/0316423 A1 | 12/2012 | Raleigh et al. | |
| 2012/0323233 A1 | 12/2012 | Maguire et al. | |
| 2013/0035682 A1 | 2/2013 | Weil | |
| 2013/0053617 A1 | 2/2013 | Pu et al. | |
| 2013/0079645 A1 | 3/2013 | Amirana et al. | |
| 2013/0211482 A1 | 8/2013 | Piipponen | |
| 2013/0237822 A1 | 9/2013 | Gross et al. | |
| 2013/0336450 A1 | 12/2013 | Kyriakou et al. | |
| 2014/0005463 A1 | 1/2014 | Jongen | |
| 2014/0107390 A1 | 4/2014 | Brown et al. | |
| 2014/0107435 A1 | 4/2014 | Sharf et al. | |

(56) References Cited

U.S. PATENT DOCUMENTS

| | | |
|---|---|---|
| 2014/0316247 A1 | 10/2014 | Hwang et al. |
| 2014/0343401 A1 | 11/2014 | Huber et al. |
| 2015/0004561 A1 | 1/2015 | Koehler |
| 2015/0080634 A1 | 3/2015 | Huber et al. |
| 2015/0092907 A1 | 4/2015 | Dong et al. |
| 2015/0112197 A1 | 4/2015 | Bharat |
| 2015/0146955 A1 | 5/2015 | Dong et al. |
| 2015/0150643 A1 | 6/2015 | Trayanova et al. |
| 2015/0182760 A1 | 7/2015 | Raleigh et al. |
| 2015/0209599 A1 | 7/2015 | Schlosser et al. |
| 2015/0290472 A1 | 10/2015 | Maguire et al. |
| 2015/0331118 A1 | 11/2015 | Iltis |
| 2015/0343238 A1 | 12/2015 | Balakin |
| 2015/0371420 A1 | 12/2015 | Yerushalmy et al. |
| 2016/0000409 A1 | 1/2016 | Bruder et al. |
| 2016/0035108 A1 | 2/2016 | Yu et al. |
| 2016/0058368 A1 | 3/2016 | Swaminathan et al. |
| 2016/0074674 A1 | 3/2016 | Kohli et al. |
| 2016/0082284 A1 | 3/2016 | Ooga et al. |
| 2016/0114189 A1 | 4/2016 | Mihailescu |
| 2016/0117850 A1 | 4/2016 | Jin et al. |
| 2016/0121142 A1 | 5/2016 | Zhang et al. |
| 2016/0125625 A1 | 5/2016 | Kim et al. |
| 2016/0184610 A1 | 6/2016 | Porikli |
| 2016/0324499 A1 | 11/2016 | Sen Sharma et al. |
| 2016/0331262 A1 | 11/2016 | Kuck et al. |
| 2016/0338676 A1 | 11/2016 | Berger et al. |
| 2016/0339271 A1 | 11/2016 | Bach et al. |
| 2016/0371862 A1 | 12/2016 | Silver et al. |
| 2017/0014642 A1 | 1/2017 | An et al. |
| 2017/0014645 A1 | 1/2017 | Foo et al. |
| 2017/0042515 A1 | 2/2017 | Schwartz et al. |
| 2017/0080253 A1 | 3/2017 | Clayton |
| 2017/0095197 A1 | 4/2017 | Kleiner et al. |
| 2017/0106208 A1 | 4/2017 | Gauthier et al. |
| 2017/0128744 A1 | 5/2017 | Adler et al. |
| 2017/0203123 A1 | 7/2017 | Requardt et al. |
| 2018/0153467 A1 | 6/2018 | Lichtenstein et al. |
| 2018/0185671 A1 | 7/2018 | Filiberti et al. |
| 2018/0214713 A1 | 8/2018 | Dehghan Marvast et al. |
| 2018/0229057 A1* | 8/2018 | Fontanarosa ........ A61N 5/1049 |
| 2018/0243584 A1 | 8/2018 | Nord et al. |
| 2018/0252825 A1 | 9/2018 | Benlloch Baviera et al. |
| 2018/0318606 A1 | 11/2018 | Robinson et al. |
| 2019/0099621 A1 | 4/2019 | Koehl et al. |
| 2019/0164288 A1 | 5/2019 | Wang et al. |
| 2019/0344098 A1 | 11/2019 | Maguire et al. |
| 2019/0351254 A1 | 11/2019 | Sumanaweera et al. |
| 2019/0380670 A1 | 12/2019 | Hofmann et al. |
| 2020/0016429 A1 | 1/2020 | Maguire et al. |
| 2020/0090345 A1 | 3/2020 | Krebs et al. |
| 2020/0113546 A1 | 4/2020 | Madore et al. |
| 2020/0151921 A1 | 5/2020 | Schildkraut |
| 2020/0179722 A1 | 6/2020 | Packer et al. |
| 2021/0012544 A1 | 1/2021 | Lee et al. |
| 2021/0015454 A1 | 1/2021 | Puleo et al. |
| 2021/0065414 A1 | 3/2021 | Do |
| 2022/0183657 A1 | 6/2022 | McLaughlin et al. |
| 2022/0386987 A1 | 12/2022 | Camps et al. |

FOREIGN PATENT DOCUMENTS

| | | | | |
|---|---|---|---|---|
| CN | 1672651 A | 9/2005 | | |
| CN | 101268467 A | 9/2008 | | |
| CN | 101600473 A | 12/2009 | | |
| CN | 102119586 A | 7/2011 | | |
| CN | 102196768 A | 9/2011 | | |
| CN | 102510735 A | 6/2012 | | |
| CN | 102781359 A | 11/2012 | | |
| CN | 103180015 A | 6/2013 | | |
| CN | 103279929 A | 9/2013 | | |
| CN | 104349817 A | 2/2015 | | |
| CN | 105813691 A | 7/2016 | | |
| CN | 106291656 A | 1/2017 | | |
| CN | 107730455 A | 2/2018 | | |
| CN | 108022272 A | 5/2018 | | |
| CN | 111223156 A | 6/2020 | | |
| DE | 102013102920 A1 | 9/2014 | | |
| DE | 102013112573 A1 | 6/2015 | | |
| DE | 102014217966 A1 | 3/2016 | | |
| EP | 0327459 B1 | 9/1992 | | |
| EP | 2140913 A1 | 1/2010 | | |
| EP | 2290406 A2 | 3/2011 | | |
| EP | 2523623 A1 | 11/2012 | | |
| EP | 2942081 A1 | 11/2015 | | |
| EP | 2950119 A1 | 12/2015 | | |
| EP | 3036978 A1 | 6/2016 | | |
| FR | 2930995 A1 | 11/2009 | | |
| FR | 3058249 A3 | 5/2018 | | |
| JP | 2005095640 A | 4/2005 | | |
| JP | 2006113061 A | 4/2006 | | |
| JP | 2007047066 A | 2/2007 | | |
| JP | 2007526010 A | 9/2007 | | |
| JP | 2010540050 A | 12/2010 | | |
| JP | 2012533364 A | 12/2012 | | |
| JP | 2016214438 A | 12/2016 | | |
| JP | 6222798 B2 * | 11/2017 | ........... | A61B 5/0006 |
| KR | 20110040164 A | 4/2011 | | |
| WO | WO-0126569 A1 | 4/2001 | | |
| WO | WO-2006114735 A1 * | 11/2006 | ........... | A61B 8/4236 |
| WO | WO-2008086434 A2 | 7/2008 | | |
| WO | WO-2009111783 A2 | 9/2009 | | |
| WO | WO-2011012154 A1 | 2/2011 | | |
| WO | WO-2011021410 A1 | 2/2011 | | |
| WO | WO-2012104416 A1 | 8/2012 | | |
| WO | WO-2012152938 A2 | 11/2012 | | |
| WO | WO-2012154219 A2 | 11/2012 | | |
| WO | WO-2013034709 A1 | 3/2013 | | |
| WO | WO-2013129811 A1 | 9/2013 | | |
| WO | WO-2013179221 A1 | 12/2013 | | |
| WO | WO-2015025203 A1 | 2/2015 | | |
| WO | WO-2015040225 A1 | 3/2015 | | |
| WO | WO-2015053737 A1 | 4/2015 | | |
| WO | WO-2016193929 A2 | 12/2016 | | |
| WO | WO-2017066358 A1 | 4/2017 | | |
| WO | WO-2017078757 A1 | 5/2017 | | |
| WO | WO-2017156113 A1 | 9/2017 | | |
| WO | WO-2019017752 A1 | 1/2019 | | |
| WO | WO-2019096943 A1 | 5/2019 | | |
| WO | WO-2020033355 A1 | 2/2020 | | |
| WO | WO-2020075106 A2 | 4/2020 | | |
| WO | WO-2020142397 A1 | 7/2020 | | |
| WO | WO-2020212573 A1 | 10/2020 | | |
| WO | WO-2021094824 A1 | 5/2021 | | |
| WO | WO-2022136925 A1 | 6/2022 | | |
| WO | WO-2024062307 A1 | 3/2024 | | |

OTHER PUBLICATIONS

Asirvatham S.J., "Advances in Catheter Ablation: A Burning Trail!," Indian Heart Journal, 2011, pp. 379-385.

Bai S., et al., "An Empirical Evaluation of Generic Convolutional and Recurrent Networks for Sequence Modeling," arXiv Prepr. arXiv:1803.01271v2, Apr. 19, 2018, 14 Pages.

Baker, et al., "Prostate Displacement During Transabdominal Ultrasound Image-Guided Radiotherapy Assessed By Real-Time Four-dimensional Transperineal Monitoring," Acta Oncologica, 2015, vol. 54, No. 9, pp. 1508-1514.

Beddar A.S., et al., "Correlation Between Internal Fiducial Tumor Motion and External Marker Motion for Liver Tumors Imaged With 4D-CT," International Journal of Radiation Oncology, Biology, Physics, vol. 67(2):630-638 (Feb. 2007).

Beltrame P., et al., "Construction and Tests of Demonstrator Modules for a 3-D Axial PET System for Brain or Small Animal Imaging," Nuclear Instruments and Methods in Physics Research A, 2011, vol. 636, pp. S226-S230, Available Online May 5, 2010.

Bert C., et al., "Motion in Radiotherapy: Particle Therapy," Physics in Medicine and Biology, 2011, vol. 56, pp. R113-R44.

Bertholet, et al., "Real-Time Intrafraction Motion Monitoring In External Beam Radiotherapy," Physics in Medicine, 2019, vol. 64, No. 15.

(56) References Cited

OTHER PUBLICATIONS

Blanck O., et al., "Dose-Escalation Study for Cardiac Radiosurgery in a Porcine Model," Int J Radiat Oncol Biol Phys., vol. 89:590-598 (Dec. 2014).
Blanck, "Radiosurgery For Ventricular Tachycardia: Preclinical And Clinical Evidence And Study Design For A German Multi-Center Multi-Platform Feasibility Trial (RAVENTA)," Clinical Research in Cardiology, 09:1319-1332 (Nov. 2020).
Boas F.E., et al., "Evaluation Of Two Iterative Techniques For Reducing Metal Artifacts In Computed Tomography," Radiology, Jun. 2011, vol. 259, No. 3, pp. 894-902.
Bode F., et al., "Pulmonary Vein Isolation by Radiosurgery: Implications for Non-Invasive Treatment of Atrial Fibrillation," Europace, vol. 17:1868-1874 (Mar. 2015).
Braem A., et al., "AX-PET: A Novel PET Detector Concept with Full 3D Reconstruction," Nuclear Instruments and Methods in Physics Research A, 2009, vol. 610, pp. 192-195, Available Online May 29, 2009.
Calkins H., et al., "2012 HRS/EHRA/ECAS Expert Consensus Statement on Catheter and Surgical Ablation of Atrial Fibrillation: Recommendations for Patient Selection Procedural Techniques, Patient Management and Follow-Up, Definitions, Endpoints, and Research Trial Design," Heart Rhythm, 2012, vol. 9(4):632-696(e21) (Apr. 2012).
Cappato R., et al., "Updated Worldwide Survey on the Methods, Efficacy, and Safety of Catheter Ablation for Human Atrial Fibrillation," Circulation: Arrhythmia and Electrophysiology, 2010, vol. 3, pp. 32-38, DOI: 10.1161/CIRCEP.109.859116.
Casella C., et al., "A High Resolution TOF-PET Concept With Axial Geometry and Digital SiPM Readout," Nuclear Instruments and Methods in Physics Research A, 2014, vol. 736, pp. 161-168.
Chaudhri, et al., "SU-E-T-334: Clinical Implementation of Gating and Dose Verification with Scanned Ion Beams at HIT," Medical Physics, The American Association of Physicists in Medicine, 39(Issue 6—Part 15):3780-3781 (Jun. 2012).
Che, et al., "Ultrasound Registration: A Review," Methods, 115:128-143 (Feb. 2017).
Constantinescu A., et al., "Catheter-Free Ablation of Atrial Fibrillation: Further Planning Studies in Patient Data Using a Scanned Carbon Ion Beam for Pulmonary Vein Isolation, MP04-02," Hearth Rhythm, May 2014, vol. 11 No. 5, Supplement.
Constantinescu A., et al., "Planning Studies for Non-Invasive Isolation of the Pulmonary Veins with a Scanned Carbon Ion Beam," Heart Rhythm, 2013, vol. 10, p. S33.
Constantinescu A., et al., "Treatment Planning Studies in Patient Data with Scanned Carbon Ion Beams for Catheter-Free Ablation of Atrial Fibrillation," Journal of Cardiovascular Electrophysiology, 2016, vol. 27, No. 3, pp. 335-344.
De Luca, et al., "The 2014 Liver Ultrasound Tracking Benchmark," Physics in Medicine & Biology, 60(14):5571 (Jul. 2015).
De Vries T., et al. "Improved Regularization of Convolutional Neural Networks with Cutout," University of Guelph, Canadian Institute for Advanced Research and Vector Institute, Nov. 29, 2017, 08 Pages.
Degiovanni A., et al., "Design of a Fast-Cycling High-Gradient Rotating Linac For Protontherapy," Proceedings of IPAC, Shanghai, China THPWA008, 2013, pp. 3642-3644.
Deisher A., et al., "Catheter-Free Ablation With External Photon Radiation: Treatment Planning, Delivery Considerations, and Correlation of Effects With Delivered Dose," Heart Rhythm, May 2015, vol. 12, No. 5, Supplement.
Del Carpio Munoz F., et al., "Three-Dimensional Mapping of Cardiac Arrhythmias: What do the Colors Really Mean?," Circulation Arrhythmia and Electrophysiology, Dec. 2010, vol. 3, No. 6, pp. e6-e11.
Deneke T., et al., "Silent Cerebral Events/Lesions Related to Atrial Fibrillation Ablation: A Clinical Review," Journal of Cardiovascular Electrophysiology, 2015, vol. 26, pp. 455-463, DOI: 10.1111/jce.12608.
Depuydt, et al., "Treating Patients With Real-Time Tumor Tracking Using The Vero Gimbaled Linac System: Implementation And First Review," Radiotherapy and Oncology, 2014, vol. 112, No. 3, pp. 343-351.
Dickfeld T., et al., "MRI-Guided Ventricular Tachycardia Ablation: Integration of Late Gadolinium-Enhanced 3D Scar in Patients with Implantable Cardioverter-Defibrillators," Circulation Arrhythmia and Electrophysiology, 2011, vol. 4, pp. 172-184. DOI: 10.1161/CIRCEP.110.958744.
Dieterich S., et al., "Respiratory Motion Management for External Beam Radiotherapy," Practical Radiation Oncology Physics, Elsevier Inc., 2016, pp. 252-263.
Dinov B., et al., "Early Referral for Ablation of Scar-Related Ventricular Tachycardia is Associated with Improved Acute and Long-Term Outcomes: Results from the Heart Center of Leipzig Ventricular Tachycardia Registry," Circulation Arrhythmia and Electrophysiology, 2014, vol. 7, pp. 1144-1151, DOI: 10.1161/CIRCEP.114.001953.
Extended European Search Report for European Application No. 18851934.2, mailed Sep. 15, 2021, 13 Pages.
Fayad, et al., "Technical Note: Correlation Of Respiratory Motion Between External Patient Surface And Internal Anatomical Landmarks," Medical Physics, 38(6):3157-3164 (Jun. 2011).
Fiorito A.M., et al., "Detection of Cardiac Events in Echocardiography Using 3D Convolutional Recurrent Neural Networks", 2018 IEEE International Ultrasonics Symposium (IUS), Oct. 22, 2018, 04 Pages, Doi:10.1109/ULTSYM.2018.8580137, XP033523144.
Fishbein M.C., et al., Early Phase Acute Myocardial Infarct Size Quantification: Validation of the Triphenyl Tetrazolium Chloride Tissue Enzyme Staining Technique, American Heart Journal, 1981, vol. 101, pp. 593-600.
Fontanarosa, et al., "Review Of Ultrasound Image Guidance In External Beam Radiotherapy: I. Treatment Planning And Inter-Fraction Motion Management," Physics in Medicine & Biology, 60(3):R77-R114 (Jan. 2015).
Franceschi F., et al., "Histopathological Effects and Evolution of Transvenous β-Radiation Applications in Right and Left Atria: An Animal Study," Europace, 2012, vol. 14, pp. 745-751, DOI: 10.1093/europace/eur351.
Ge J., et al., "Planning 4-Dimensional Computed Tomography (4DCT) Cannot Adequately Represent Daily Intrafractional Motion of Abdominal Tumors," International Journal of Radiation Oncology, Biology, Physics, vol. 85(4):999-1005 (Mar. 2013).
Gerstenfeld E.P., "Recurrent Ventricular Tachycardia after Catheter Ablation in Post-Infarct Cardiomyopathy: "Failure" of Ablation or Progression of the Substrate?," Journal of the American College of Cardiology, 2013, vol. 61, pp. 74-76, DOI: 10.1016/j.jacc.2012.07.057.
Graeff C., et al., "A 4D-Optimization Concept for Scanned Ion Beam Therapy," Radiotherapy and Oncology, Available Online Oct. 31, 2013, vol. 109, pp. 419-424.
Graeff C., et al., "Motion Mitigation in Intensity Modulated Particle Therapy by Internal Target Volumes Covering Range Changes," Medical Physics, 2012, vol. 39, pp. 6004-6013.
Graeff, et al., "Noninvasive Cardiac Arrhythmia Ablation With Particle Beams," Medical Physics, vol. 45, No. 11 (Nov. 2018).
Grimm J., et al., "Dose Tolerance Limits and Dose Volume Histogram Evaluation for Stereotactic Body Radiotherapy," Journal of Applied Clinical Medical Physics, vol. 12(2): 267-292 (Jan. 2011).
Guerra P.G., et al., "Beta-Radiation for the Creation of Linear Lesions in the Canine Atrium," Circulation, 2004, vol. 110, pp. 911-914, DOI: 10.1161/01.CIR.0000139865.39885.03.
Haberer T., et al., "Magnetic Scanning System for Heavy ion Therapy," Nuclear Instruments and Methods A, 1993, vol. 330, pp. 296-305.
Hartman J., et al., "Dosimetric Feasibility of Intensity Modulated Proton Therapy in a Transverse Magnetic Field of 1.5 T," Physics in Medicine and Biology, 2015, vol. 60, pp. 5955-5969.
Hoogeman, et al., "Clinical Accuracy Of The Respiratory Tumor Tracking System Of The Cyberknife: Assessment By Analysis Of Log Files," International Journal of Radiation Oncology, Biology, Physics, 2009, vol. 74, No. 1, pp. 297-303, DOI: 10.1016/j.ijrobp.2008.12.041, XP026037471.

(56) References Cited

OTHER PUBLICATIONS

Iguchi T., et al., "Development of Compact Compton Gamma Camera for Non-Destructive Detection and Location of Hidden Explosives with Neutron Induced Prompt Gamma-Ray Imaging," Nuclear Science Symposium Conference Record, IEE Wyndham El Conquistador Resort, Puerto Rico, Piscataway, NJ, USA, IEEE, Oct. 23-29, 2005, vol. 2, pp. 735-739, DOI:10.1109/NSSMIC.2005. 1596362, ISBN 978-0-7803-9221-2, XP010895599.
International Search Report & Written Opinion dated Dec. 11, 2023 in Int'l PCT Patent Appl. Serial No. PCT/IB2023/058539 (0710).
International Search Report and Written Opinion for International Application No. PCT/EP2018/081455, mailed Feb. 12, 2019, 13 Pages.
International Search Report and Written Opinion for International Application No. PCT/IB2019/058638, mailed Jun. 25, 2020, 17 Pages.
International Search Report and Written Opinion for International Application No. PCT/IB2020/000930, mailed Apr. 9, 2021, 11 Pages.
International Search Report and Written Opinion for International Application No. PCT/IB2021/000922, mailed Apr. 19, 2022, 15 Pages.
International Search Report and Written Opinion for International Application No. PCT/US2018/049114, mailed Nov. 21, 2018, 09 Pages.
Ipsen, et al., "Radiotherapy Beyond Cancer: Target Localization In Real-time MRI And Treatment Planning For Cardiac Radiosurgery," Medical Physics, vol. 41(12):120702_1-120702_8 (Dec. 2014).
Ipsen, et al., "Target Tracking Accuracy And Latency With Different 4D Ultrasound Systems—A Robotic Phantom Study," Current Directions in Biomedical Engineering, 6(1):20200038 (Sep. 2020).
Ipsen, S., "See What You Treat: 4d Ultrasound Imaging For Real Time Motion Compensation In The Liver," PhD Thesis University of Luebeck, pp. 1-142 (Nov. 2019).
Kachelriess M., et al., "ECG-Correlated Image Reconstruction from Subsecond Multi-Slice Spiral CT Scans of the Heart," Medical Physics, 2000, vol. 27, pp. 1881-1902.
Keall et al., "The Management of respiratory motion in radiation on oncology report of AAPM Task Group $76^{a)}$ ," Med. Phys., vol. 33(10):3874-3900 (Oct. 2006).
Keall P.J, et al., "The First Clinical Implementation of Electromagnetic Transponder-Guided MLC Tracking," Medical Physics, 2014, vol. 41: 020702.
Keall P.J., et al., "The First Clinical Treatment with Kilovoltage Intrafraction Monitoring (KIM): A Real-Time Image Guidance Method," Medical Physics, 2015, vol. 42, pp. 354-358.
Khalil, et al., "An Overview on Image Registration Techniques for Cardiac Diagnosis and Treatment," Cardiology Research and Practice, 2018, Article ID 1437125, 15 pages, https://doi.org/10.1155/2018/1437125.
Kincaid, et al., "Investigation Of Gated Cone-Beam CT To Reduce Respiratory Motion Blurring," Medical Physics, 40(4):041717 (Apr. 2013).
Kingma D.P., et al., "Adam: A Method for Stochastic Optimization," Published as a Conference Paper at ICLR, arXiv: 1412. 6980v8, Jul. 23, 2015, pp. 1-15.
Klein E.E., et al., "Task Group 142 report: Quality assurance of medical accelerators," Medical Physics, The American Association of Physicists in Medicine, Sep. 2009, vol. 36, No. 9, pp. 4197-4212, Published on Aug. 17, 2009.
Koike Y., et al., "Deep Learning-Based Metal Artifact Reduction Using Cycle-Consistent Adversarial Network For Intensity-Modulated Head And Neck Radiation Therapy Treatment Planning," Physica Medica, Sep. 7, 2020, vol. 78, pp. 8-14.
Krimmer J., et al., "Prompt-Gamma Monitoring in Hadrontherapy: A Review," Nuclear Instruments and Methods in Physics Research A, 2018, vol. 878, pp. 58-73, Available online Aug. 12, 2017.
Kumar S., et al., "Effect of Respiration on Catheter-Tissue Contact Force during Ablation of Atrial Arrhythmias," Heart Rhythm, vol. 9(7):1041-1047e1 (Jul. 2012).

Kuntz J., et al., "Fully Automated Intrinsic Respiratory and Cardiac Gating for Small Animal CT," Physics in Medicine and Biology, vol. 55:2069-2085 (Apr. 2010).
Lachaine, et al., "Intrafractional Prostate Motion Management With The Clarity Autoscan System," Medical Physics International Journal, 1(1):72-80 (2013).
Lehmann H.I., et al., "Atrioventricular Node Ablation in Langendorffperfused Porcine Hearts using Carbon Ion Particle Therapy: Methods and an in Vivo Feasibility Investigation for Catheter-Free Ablation of Cardiac Arrhythmias," Circulation Arrhythmia and Electrophysiology, Apr. 2015, vol. 8, pp. 429-438, DOI: 10.1161/ CIRCEP.114.002436.
Lehmann H.I., et al., "Biophysics of Tissue Ablation in Catheter-Free Ablation With Carbon Ion Beams," vol. 13:(5):AB29-05 S67 (May 1016).
Lehmann H.I., et al., "Delineation of Target Locations and Organs at Risk for Particle Beam Therapy: Atlas for Extracorporeal CT-Based Ablation of Cardiac Tissue," Heart Rhythm, May 2017 vol. 11, No. 5, Supplement.
Lehmann H.I., et al., "External Arrhythmia Ablation using Photon Beams: Ablation of the Atrioventricular Junction in an Intact Animal Model," Circulation: Arrhythmia and Electrophysiology, Apr. 2017, vol. 10, No. 4 (e004304).
Lehmann H.I., et al., "Feasibility Study on Cardiac Arrhythmia Ablation Using High-Energy Heavy Ion Beams," Nature, Scientific Reports, Dec. 20, 2016, vol. 6, No. 38895, 13 Pages, DOI: 10.1038/srep38895.
Lehmann H.I., et al., "In-Beam PET Verification of Catheter-Free Arrhythmia Ablation by Scanned Carbon-12 Ion Beam Irradiation," Circulation, 2015, vol. 132, Supplement. 3, p. A12443.
Li, et al., Comparative Quantitative Analysis of Robotic Ultrasound Image Calibration Methods, 2021 20th International Conference on Advanced Robotics (ICAR), IEEE, pp. 511-516.
Lin M.H., et al., "4D Patient Dose Reconstruction using Online Measured EPID Cine Images for Lung SBRT Treatment Validation," Medical Physics, 2012, vol. 39, pp. 5949-5958.
Lis M., et al., "A Modular Dose Delivery System For Treating Moving Targets With Scanned Ion Beams: Performance And Safety Characteristics, and Preliminary Tests," Physica Medica, 2020, vol. 76, pp. 307-316.
Luzhbin D., et al., "Model Image-Based Metal Artifact Reduction for Computed Tomography," Journal of Digital Imaging, 2020, vol. 33, pp. 71-82.
Maguire., et al., "First-In-Man Cardiac Radiosurgery for Atrial Arrhythmia," International Journal of Radiation Oncology, Biology, Physics, 96(2):E504-5 (Oct. 2016).
Maguire P., et al., "Cardiac Radiosurgery (CyberHeart) for Treatment of Arrhythmia: Physiologic and Histopathologic Correlation in the Porcine Model," Cureus, 3(8):(e32) (Aug. 2011).
Nakao M., et al., "Regularized Three-Dimensional Generative Adversarial Nets for Unsupervised Metal Artifact Reduction in Head and Neck CT Images," IEEE Access, Digital Object Identifier, Jun. 12, 2020, vol. 8, pp. 109453-109465.
Nankali, et al., "Geometric And Dosimetric Comparison Of Four Intrafraction Motion Adaptation Strategies For Stereotactic Liver Radiotherapy," Physics in Medicine & Biology, 63(14):145010 (Jul. 2018).
Ng J., et al., "Mapping of Dominant Activation Directions in a Canine Rapid Atrial Pacing Model of Atrial Fibrillation," Heart Rhythm Session, May 12, 2017.
O'Shea, et al., "Review Of Ultrasound Image Guidance In External Beam Radiotherapy Part II: Intra-Fraction Motion Management And Novel Applications," Physics in Medicine & Biology, 2016, vol. 61, No. 8, DOI: 10.1088/0031-9155/61/8/R90, XP020303407.
Okumura Y., et al., "Three-Dimensional Ultrasound for Image-Guided Mapping and Intervention: Methods, Quantitative Validation, and Clinical Feasibility of a Novel Multimodality Image Mapping System," Circulation Arrhythmia Electrophysiology, 2008, vol. 1, pp. 110-119, DOI: 10.1161/ CIRCEP.108.769935.
Ortega P.G., et al., "Noise Evaluation of Compton Camera Imaging for Proton Therapy," Physics in Medicine and Biology, Institute of

(56) References Cited

OTHER PUBLICATIONS

Physics Publishing and Engineering in Medicine, Bristol, GB, Feb. 6, 2015, vol. 60, No. 5, pp. 1845-1863, DOI:10.1088/0031-9155/60/5/1845, ISSN 0031-9155.

Ortmaier T., et al., "Motion Estimation in Beating Heart Surgery," IEEE Transactions on Biomedical Engineering, 2005, vol. 52, pp. 1729-1740.

Pan J., et al., "A Real-Time QRS Detection Algorithm," IEEE Transactions on Biomedical Engineering, Mar. 1985, vol. BME-32, No. 3, pp. 230-236.

Partial Supplementary European Search Report for European Application No. 18851934.2, mailed Apr. 22, 2021, 11 Pages.

Perali I., et al., "Prompt Gamma Imaging of Proton Pencil Beams at Clinical Dose Rate," Institute of Physics and Engineering in Medicine, Physics in Medicine and Biology, Sep. 10, 2014, vol. 59, pp. 5849-5871.

Peulen H., et al., "Mid-Ventilation Based PTV Margins in Stereotactic Body Radiotherapy (SBRT): A Clinical Evaluation," Radiotherapy and Oncology, vol. 110:(3):511-516, DOI: 10.1016/j.radonc.2014.01.010 (Mar. 2014).

Pfanner F., et al. "Monitoring Cardiac Motion in CT using a Continuous Wave Radar Embedded in the Patient Table," Medical Physics, 2014, vol. 41: 081908.

Pfanner F., et al., "Monitoring internal organ motion with continuous wave radar in CT," Medical Physics, 2013, vol. 40: 091915.

Piersanti L., et al., Measurement of Charged Particle Yields from PMMA Irradiated by a 220 MeV/u (12)C Beam, Physics in Medicine and Biology, 2014, vol. 59, pp. 1857-1872.

Poon, et al., "Technical Note: Cardiac Synchronized Volumetric Modulated Arc Therapy for Stereotactic Arrhythmia Radioablation—Proof of Principle," Medical Physics, vol. 47(8):3567-3572 (Aug. 2020).

Poulsen P.R., et al., "A Method of Dose Reconstruction for Moving Targets Compatible with Dynamic Treatments," Medical Physics, vol. 39(10):6237-6246 (Oct. 2012).

Poulsen P.R., et al., "Kilovoltage Intrafraction Motion Monitoring and Target Dose Reconstruction for Stereotactic Volumetric Modulated Arc Therapy of Tumors in the Liver," Radiotherapy and Oncology, 2014, vol. 111, pp. 424-430.

Prall M., et al., "Ion Beam Tracking Using Ultrasound Motion Detection," Medical Physics, 41(4):041708-1-041708-5 (Apr. 2014).

Prall M., et al., "Treatment of Arrhythmias by External Charged Particle Beams: A Langendorff Feasibility Study," Biomedical Engineering—Biomedical Technology, Published Online On Feb. 19, 2015, vol. 60, No. 2, pp. 147-156.

Pérez-Castellano N., et al., "Pathological Effects of Pulmonary Vein Beta-Radiation in a Swine Model," Journal of Cardiovascular Electrophysiology, 2006, vol. 17, pp. 662-669, DOI: 10.1111/j.1540-8167.2006.00462.x.

Queiros, et al., "Fast Left Ventricle Tracking Using Localized Anatomical Affine Optical Flow," International Journal for Numerical Methods in Biomedical Engineering, 33(11):e2871 (Nov. 2017).

Raaymakers B.W., et al., "Integrating a 1.5 T MRI Scanner With A 6 MV Accelerator: Proof of Concept," Physics in Medicine and Biology, 54(12):N229-N37 (May 2009).

Ravkilde T., et al., "Time-Resolved Dose Distributions to Moving Targets During Volumetric Modulated Arc Therapy With And Without Dynamic MLC Tracking," Medical Physics, 2013, 40(11):111723-1-111723-8 (Nov. 2013).

Rettmann M.E., et al., "Analysis of Left Atrial Respiratory and Cardiac Motion for Cardiac Ablation Therapy," Medical Imaging 2015: Image-Guided Procedures, Robotic Interventions, and Modeling, 9415:651-656 ) Mar. 2015.

Rettmann M.E., et al., "Centerline Tracking for Quantification of Reverse Structural Remodeling of the Pulmonary Veins Following Cardiac Ablation Therapy," Academic Radiology, 19(11):1332-1344 (Nov. 2012).

Richter C., et al., "First Clinical Application of a Prompt Gamma Based in Vivo Proton Range Verification System," Radiotherapy and Oncology, vol. 118(2):232-237 (Feb. 2016).

Richter D., et al., "ECG-Based 4d-Dose Reconstruction of Cardiac Arrhythmia Ablation With Carbon Ion Beams: Application in a Porcine Model," Physics in Medicine and Biology, Aug. 4, 2017, vol. 62, No. 17, p. 6869.

Richter D., et al., "Four-Dimensional Patient Dose Reconstruction for Scanned Ion Beam Therapy of Moving Liver Tumors," International Journal of Radiation Oncology, Biology, Physics, 2014, vol. 89, pp. 175-181.

Richter D., et al., "Residual Motion Mitigation in Scanned Carbon Ion Beam Therapy of Liver Tumors Using Enlarged Pencil Beam Overlap," Radiotherapy and Oncology, vol. 113, pp. 290-295 (Nov. 2014).

Richter D., et al., "Upgrade and Benchmarking of A 4D Treatment Planning System for Scanned Ion Beam Therapy," Medical Physics, vol. 40:051722 (May 2013).

Robinson, et al., "An Evaluation Of The Clarity 3D Ultrasound System For Prostate Localization," Journal of Applied Clinical Medical Physics, 13(4):100-112 (Jul. 2012).

Roujol, et al., "Characterization Of Respiratory And Cardiac Motion From Electro-Anatomical Mapping Data For Improved Fusion Of MRI To Left Ventricular Electrograms," PloS One, 2013, vol. 8, No. 11, p. e78852.

Saint-Gobain Ceramics & Plastics Inc: "Scintillation Materials and Assemblies, About Saint-Gobain Crystals," Saint-Gobain Crystals Handbook, 2004-2019, 12 Pages.

Sauli F., "Radiation Imaging with Gaseous Detectors," Nuclear Instruments and Methods in Physics Research A, 2018, vol. 878, pp. 1-9.

Scandurra D., et al., "Assessing the Quality of Proton PBS Treatment Delivery Using Machine Log Files: Comprehensive Analysis of Clinical Treatments Delivered at PSI Gantry 2," Physics in Medicine and Biology, vol. 61, pp. 1171-1181 (Jan. 2016).

Schardt D., et al., "Heavy-Ion Tumor Therapy: Physical and Radiobiological Benefits," Reviews of Modern Physics, vol. 82(1):383-425 (Mar. 2010).

Schlosser J., et al., "Radiolucent 4D Ultrasound Imaging: System Design and Application to Radiotherapy Guidance," IEEE Transactions on Medical Imaging, Oct. 2016, vol. 35, No. 10, pp. 2292-2300.

Shackleford J.A., et al., "On Developing B-Spline Registration Algorithms for Multi-Core Processors," Phys. Med. Biol., vol. 55, pp. 6329-6351 (Oct. 2010).

Sharma A., et al., "New Non-Invasive Therapy for Cardiac Arrhythmias using Stereotactic Radiosurgery: Initial Feasibility Testing," Heart Rythm, vol. 4(5):S68, Abstract (May 2007).

Sharma A., et al., "Non-Invasive Ablation of the Left Superior Pulmonary Vein-Left Atrial Junction Using Stereotactic Focused Radiation," Circulation, vol. 116:489, Abstract (Oct. 2007).

Sharma A., et al., "Non-Invasive Approach to Myocardial Ablation: Pathology Of Stereotactic Robot Targeted High Energy X-Ray Lesions at Potential Arrhythmia Sites," Heart Rhythm, vol. 5(5): S67 (AB32-3), Abstract (May 2008).

Sharma A., et al., "Noninvasive Stereotactic Radiosurgery (CyberHeart) for Creation of Ablation Lesions in the Atrium," Heart Rhythm, 2010, vol. 7, pp. 802-810, DOI: 10.1016/j.hrthm.2010.02.010.

Smith, Scott, Ultrasound Miniaturization, 2011 Joint AAPM / COMP Meeting Jul. 31-Aug. 4, 2011, Vancouver, available at: https://www.aapm.org/meetings/amos2/pdf/59-17269-42515-909.pdf.

Soejima K., et al., "Catheter Ablation in Patients With Multiple and Unstable Ventricular Tachycardias after Myocardial Infarction: Short Ablation Lines Guided by Reentry Circuit Isthmuses and Sinus Rhythm Mapping," Circulation, 2001, vol. 104, pp. 664-669.

Soejima K., et al., "Endocardial and Epicardial Radiofrequency Ablation of Ventricular Tachycardia Associated With Dilated Cardiomyopathy: The Importance of Low-Voltage Scars," Journal of American College of Cardiology, 2004, vol. 43, pp. 1834-1842, DOI: 10.1016/j.acc.2004.01.029.

Solevi P., "Study of an In-Beam PET System for CNAO, the National Centre for Oncological Hadrontherapy," PHD Thesis, Milano University, 2007, pp. 1-142 (144 Pages).

(56) References Cited

OTHER PUBLICATIONS

Sosnovik D.E., et al., "Magnetic Nanoparticles for MR Imaging: Agents, Techniques And Cardiovascular Applications," Basic Research in Cardiology, 2008, vol. 103, No. 2, pp. 122-130.
Suleiman M., et al., "The Noncoronary Cusp as a Site for Successful Ablation of Accessory Pathways: Electrogram Characteristics in Three Cases," Journal of Cardiovascular Electrophysiology, 2010.
Takami M., et al., "Effect of Left Atrial Ablation Process and Strategy on Microemboli Formation During Irrigated Radiofrequency Catheter Ablation in an In Vivo Model," Circulation. Arrythmia and Electrophysiology, 2016, vol. 9:e003226, DOI: 10.1161/CIRCEP.115.003226.
Topolnjak, et al., "Image-Guided Radiotherapy For Left-sided Breast Cancer Patients: Geometrical Uncertainty Of The Heart," International Journal of Radiation Oncology, Biology, Physics, 82(4):e647-e655 (Mar. 2012).
Uhl M., et al., "High Control Rate in Patients With Chondrosarcoma of the Skull Base After Carbon Ion Therapy: First Report of Long-Term Results," Cancer, 2014, vol. 120, pp. 1579-1585.
Van Der Ree, et al., "Cardiac Radioablation—A Systematic Review," Heart Rhythm, vol. 17(8):1381-1392 (Aug. 2020).
Watts D.A., "Detectors for Quality Assurance in Hadrontherapy," Doctoral Thesis, University of Barcelona, May 30, 2013, 265 Pages.
Wellenberg R.H.H., et al., "Metal Artifact Reduction Techniques In Musculoskeletal CT-Imaging," European Journal of Radiology, 2018, vol. 107, pp. 60-69.
Yu L., et al., "Autonomic Denervation With Magnetic Nanoparticles," Circulation, 2010, vol. 122, pp. 2653-2659.
Zei P.C., et al., "Ablative Radiotherapy as a Noninvasive Alternative to Catheter Ablation for Cardiac Arrhythmias," Current Cardiology Reports, Published Online On Jul. 27, 2017, Nov. 1, 2018, vol. 19, No. 79, pp. 1-9, XP036310567, Retrieved from URL: https://www.ncbi.nlm.nih.gov/pmc/articles/PMC5532420.

\* cited by examiner

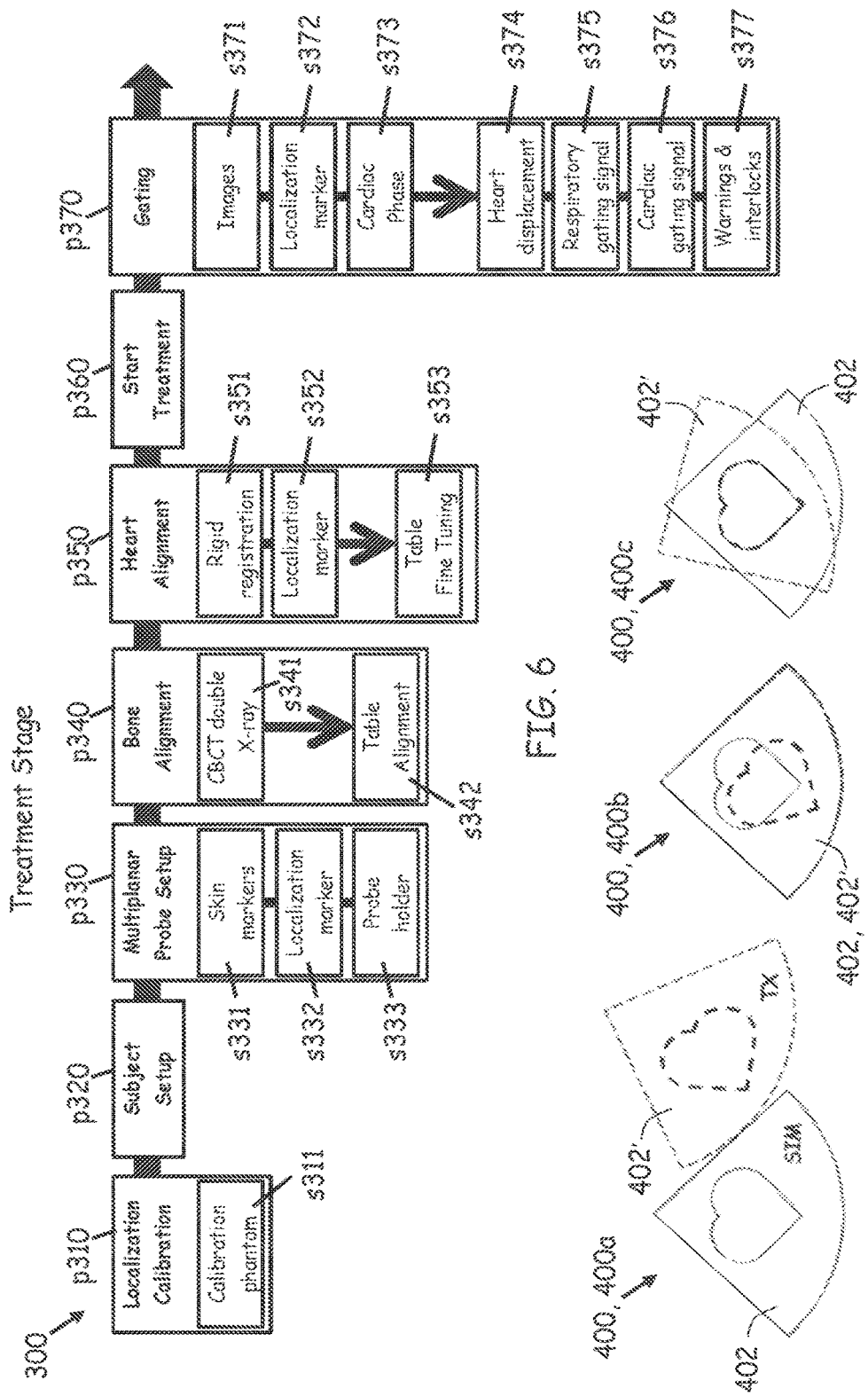

MULTIPLANAR MOTION MANAGEMENT SYSTEM

RELATED APPLICATIONS

This application is a continuation of U.S. patent application Ser. No. 18/269,351, filed Jun. 23, 2023, which is a national phase application under 35 U.S.C. § 371 of PCT/IB2021/000922, filed Dec. 23, 2021, which claims the benefit of priority of U.S. Provisional Patent Application Ser. No. 63/129,694, filed Dec. 23, 2020, the entire contents of each of which are incorporated herein by reference.

FIELD OF THE DISCLOSURE

This disclosure is directed generally to devices and techniques for external beam therapy, and more specifically to non-invasive treatment of cardiac arrhythmias.

BACKGROUND OF THE DISCLOSURE

Cardiac arrhythmias are disruptions in the normal heartbeat. They affect more than two percent of the general population in Europe and are expected to at least double in the next 50 years as the population ages. Their occurrence is strongly linked to an increased risk of heart attacks and strokes.

More particularly, heart arrhythmia is a problem with the rate or rhythm of the heartbeat. The heart beats too quickly, too slowly, or with an irregular pattern. When at rest, the heart beating faster than normal, above 100 beats per minute in adults, is called tachycardia. The heart beating too slowly, below 60 beats per minute, is called bradycardia. A common type of arrhythmia is atrial fibrillation, which causes an irregular and fast heartbeat. Many factors can affect the rhythm of the heart such as having had a heart attack, smoking, congenital heart defects, and stress. Some substances or medicines may also cause arrhythmias.

Treatments may include medications, medical procedures such as ablation therapy or implantation of a pacemaker or defibrillator, and surgery. Medications for a fast heart rate may include beta-blockers or agents that attempt to restore a normal heart rhythm such as procainamide. Medications may have more significant side effects especially if taken for a long period of time. Pacemakers are often used for slow heart rates. Those with an irregular heartbeat are often treated with blood thinners to reduce the risk of complications. Those who have severe symptoms from an arrhythmia may receive urgent treatment with a controlled electric shock in the form of cardioversion or defibrillation.

Ablation therapies are often used to treat arrhythmias. Ablation therapies include burning or freezing specific heart tissues with invasive tools such as catheters, to stop the conduction of the disrupted electrical signals in these specific tissues. Invasive catheter ablation procedures are surgical interventions performed manually and the treatment efficacy varies largely from 50% to 80% depending on the technology used and skill of the surgeon. Moreover, the procedures can involve several medical staff members and can require many hours, during which patients are at risk of serious complications like tissue perforation, vein stenosis, or creation of a blood clot. The nature of the lesions created by catheter ablation results in procedures which are often repeated successive times, with increasing complexity for the medical staff and risk for the patient.

There is therefore a need for methods of treatment using non-invasive devices for treatment of cardiac arrhythmias via non-invasive ablation. The use of external therapy beams, including but not limited to charged particle beams, photon beams, proton beams, and carbon and helium ions, offer non-invasive techniques for cardiac ablation. Improvement of devices and methods for such external beam therapies that take into account body motion of the patient in real would be welcomed.

SUMMARY OF THE DISCLOSURE

Various embodiments of the disclosure enable an accurate setup of patients and beam delivery for external therapy beams based on the position of the patient's heart. This can be beneficial not only for cardiology patients, but also, for example, for lung cancer patients undergoing radiotherapy where the heart might be an organ at risk that should be tracked during the treatment. The disclosed devices and techniques expand upon International Patent Application No. PCT/US2020/060054 to Garonna et al. ("Garonna et al."), entitled "Cardiac Phase Gating System for Radiation Therapy," filed Nov. 11, 2020 and owned by the owner of the present application. The present disclosure expands on Garonna et al. by providing an improved method for identifying the respiratory motion phase and to determine an absolute heart position in a known coordinate system in three dimensional space. Various embodiments of the disclosure track the heart motion without the segmentation of any anatomical landmarks (or fiducials) in the image to determine the target motion phase and position. Such techniques also do not require the co-registration or fusion of ultrasound with MRI or CT images, thereby avoiding the inaccuracies and execution time requirements associated with registration across different modalities. The presently disclosed devices and techniques are therefore advantageous in that the image processing and motion measurement is fully automatic (no operator or clinician involvement), reproducible, and faster than conventional motion control systems.

In some embodiments, external motion of the patient's thorax as detected with a surrogate is combined with the internal motion of the heart as detected by a multiplanar probe that generates multiplanar (non-parallel) images to better understand how the heart moves due to respiratory motion. The combination of external and internal motion detection enables extraction of a respiratory motion pattern from images of the heart. The devices and techniques disclosed are further able to determine the position of cardiac structures in a known three-dimensional coordinate system by a combination of multiplanar images and a probe localization system. In addition, the techniques disclosed are robust enough to detect and quantify using images the heart drift that may occur during external beam therapy.

Some embodiments provide robustness in terms of image quality (e.g., ultrasound) by enabling imaging from different thorax positions (in particular, parasternal and apical viewing windows) depending on the patient's anatomy. Also the image processing methods are designed with image quality robustness in mind. This can be beneficial for patients of advanced age or having higher body mass index, common for arrhythmia patients, which can lead to ultrasound images of less contrast due to a low echogenicity.

Various embodiments of the disclosure include redundancies which are inherently part of the design. For example, in the case of cardiac-phase recognition failure in the imaging system, the cardiac phase-gating can still be performed using the ECG signal. In another example, a localization marker on the multiplanar probe may be utilized to track external motion to enable respiratory phase gating in case of such failure in the imaging system.

Various embodiments of the disclosure enhance alignment of a treatment patient with the particle beam. Standard clinical practice involves alignment using bony anatomy. In some embodiments, this bony anatomy alignment is complemented with a heart alignment setup using ultrasound imaging.

Various embodiments of the disclosure present a system and methods for cardiac ultrasound three-dimensional motion management. A multiplanar ultrasound probe is utilized and dedicated image processing methods are disclosed for determining the position and motion of the heart in three dimensions in an accurate and fast fashion before and during external beam therapy. In some embodiments, a method is disclosed that enables accurate patient positioning based on the heart position, monitoring of potential drift in heart position during a long treatment session and monitoring of respiratory motion during treatment.

The disclosed device and methods are beneficial for the non-invasive treatment of heart arrhythmias. However, its use can also apply favorably for cancer treatments in the mediastinum and thoracic regions (breast, lung, among others), as in these cases, the precision of the treatment is affected by the position and motion of the heart, especially in the case of pencil-beam scanned particle therapy. Indeed, for these clinical applications, the heart is not the target but an important sensitive organ that clinicians want to spare, to avoid serious side-effects related to radiation.

The disclosed device and methods can also be applied outside the field of external beam radiotherapy, for example, in radiology and interventional cardiology. For radiology, it can provide means to obtain better image quality using magnetic resonance imaging (MRI), computed tomography (CT) or other medical imaging modalities, for which the heart motion (due to respiration or heartbeat) can affect the image quality and therefore influence the derived measurements and diagnosis. This would allow for, for example, avoiding the use of breath-hold or forced ventilation techniques to limit respiratory motion. For interventional cardiology, it can provide means to monitor the heart motion during the intervention. This enables the interventional cardiologist to acquire, for example, X-ray images used to visualize a catheter only at a specific cardiac or respiratory state of interest (motion phase). This would allow for a more efficient use of X-ray imaging, which reduces the radiation dose delivery to both the patient and medical staff as well as operational costs.

In some embodiments, the disclosed device and methods utilize B-mode ultrasound imaging. However, other imaging techniques are contemplated, for example, Doppler, Elastography, M-mode imaging and several other ultrasound imaging modalities. Also, the present disclosure is based on biplane ultrasound imaging that utilizes orthogonal planes; however, one of ordinary skill in the art, in view of this disclosure, may incorporate and adapt imaging techniques more generally, for example, biplane images which are not orthogonal, triplane imaging, full volumetric imaging or any other multiplanar ultrasound imaging geometry in three-dimensional space.

Conventional systems and procedures for the augmentation and execution of external beam radiation therapy treatments (radiotherapy, proton therapy, carbon ion therapy, among others) are subject to certain shortcomings. Examples where shortcomings are limiting in present day systems include patient setup, organ drift during treatment, accounting for respiratory motion, and tracking anatomical structures in three-dimensional space.

Consider the challenges of patient positioning for external beam radiation therapy treatment of the heart. Prior to the start of a course of external beam radiation therapy treatment, a computed tomography (CT) scan of the patient is typically acquired at the so-called simulation stage. Subsequently, a patient-specific treatment plan is designed based on this CT scan, after which the treatment stage can start, but generally not on the same day. During the treatment stage, the position of the patient during the simulation stage is reproduced in the treatment room to ensure the validity of the treatment plan and the beam parameters programmed for the treatment delivery. Immobilization devices, such as thermoplastic masks, standard-sized wedges, wing boards and grab bars, are typically used to assist with patient positioning for thoracic treatments. Technologies currently available to assist with this patient setup include bi-planar X-ray images, cone-beam CT or CT-on-rails. The patient alignment in the treatment room is mostly based on matching of bony anatomy (both using manual and (semi-) automatic image registration) and matching of any soft tissue close to the target which has sufficient contrast on these images (e.g., tomographic imaging). The contrast of soft tissues such as the heart on these images is typically poor. Also, the position of the heart does not always correlate well with the bony anatomy. In addition, the heartbeat and the respiratory motion of the patient further reduce the image quality. The image quality can also be affected by image artifacts created by metallic objects commonly present in the area of interest (pacemaker leads, implanted defibrillator leads, among others). Accordingly, the setup of arrhythmia patients and thorax patients in general suffers from the limited anatomical information available on the acquired images and consequently relies heavily on the judgment of the medical staff members.

Consider also the phenomenon and effect of heart drift. During external beam therapy treatment of heart arrhythmias, a radiation dose in the range of 25-40 Gy may be delivered in a single treatment fraction. This is at least 2-3 times the typical stereotactic ablative radiotherapy dose for small thoracic lesions. In addition, special methods may be used during the treatment to mitigate the effect of respiratory and cardiac motion on the treatment accuracy. Both aspects (high dose requirement and motion mitigation) result in considerably longer treatment times, with the patient typically immobilized in supine position. As such, anatomical structures in the thorax/abdomen relax, which can result in a positional drift of the target over time, herein referred to as "heart drift." While methods are emerging for efficient intra-fraction motion management, such as the MR-LINAC, there is no standard method to monitor this drift during the treatment without interrupting the radiation beam delivery, which increases the treatment time even further.

The effects of the respiratory cycle must also be managed. The cyclical heart motion is characterized by two primary components: heartbeat (with cycle period 0.5-1.5 seconds) and respiration (with cycle period of 3-5 seconds). Previous work directed to such characterization includes Garonna et al., which outlined the respiratory component but was focused on heartbeat motion aspects. For respiratory motion monitoring, systems are commercially available which indirectly monitor the internal motion of anatomical structures such as the heart by following external surrogates. These systems are either based on the flow of air into and out of the lungs (e.g., with spirometers, such as utilized by the Active Breathing Coordinator, or "ABC," device supplied by Elekta AB, Stockholm, Sweden) or the mechanical motion of the abdomen/thorax resulting from contraction of the diaphragm, such as pressure belts (e.g., the ANZAI BELT (AZ-733VI) supplied by Anzai Medical Co., Ltd. of Tokyo, Japan), optical tracking of thorax motion (e.g. the RGSC system supplied by Varian Medical Systems, Inc. of Palo Alto, California, U.S.A.), and x-ray tracking systems (e.g., the tracking system in VERO® SBRT, supplied by Brainlab AG of Munich, Germany). These approaches make assumptions about how the motion of the surrogate correlates with the internal motion of the anatomical structures and, thus, also of the behavior of the treatment target. If this correlation is weak, this may result in a poor monitoring accuracy of the target respiratory motion. Robotic radiosurgery systems (e.g., the CYBERKNIFE®, supplied by Accuray Inc. of Sunnyvale, CA, U.S.A.) are able to manage intra-fractional respiratory motion. However, its use for the heart would require implanting fiducial clips.

Several approaches are described in literature which facilitate the tracking of a treatment target on three-dimensional ultrasound volumes, which have been acquired of a specific anatomical structure or region of interest. Examples of clinically available systems are the CLARITY® and the CLARITY® AUTOSCAN systems (supplied by Elekta AB, Stockholm, Sweden). In certain applications, tracking a target in three-dimensional space requires volumetric imaging. Such requirement arises, for example, when the target can move out of the imaging plane, which would not necessarily be detected with two-dimensional imaging, thereby resulting in faulty tracking. However, tracking a target in three-dimensional space on three-dimensional ultrasound volumes suffers from a number of limitations:

Existing commercial and research grade three-dimensional ultrasound systems have inadequate spatial and time resolution.

There is a need, sometimes manually, to identify the target or a surrogate of the target whose motion correlates well with the target motion in the ultrasound volume Three-dimensional ultrasound imaging technology is bulky and expensive.

We estimate that a system comprised of conventional technology for tracking anatomical structures inside the heart in three-dimensional space would have, at best, the following performance characteristics:

Reaction time (time between the appearance of an event and the final response of the system) would be about 250 milliseconds (ms). This is composed of 200 ms for three-dimensional ultrasound volume acquisition, beam forming and data streaming from the ultrasound device to a host computer and 50 ms for data interpretation.

Spatial uncertainty for the target localization is about 6.5 mm, a combination of: 1 mm for ultrasound image localization in absolute room coordinates; 2.5 mm for segmentation and tracking accuracy of a target or a surrogate where the target itself cannot be properly tracked; 2 mm for motion correlation between the target and the surrogate of the target; and 1 mm for anatomical structure visualization differences between the planning CT scan and the ultrasound volume.

Such performance characteristics are inadequate for external radiotherapy treatment of the heart, where a reaction time of 100 ms or better and a spatial accuracy of 3 mm is expected.

The present disclosure presents hardware and software components and methods for overcoming certain present-day limitations. In addition, various clinical workflows are also disclosed.

In some embodiments, an ultrasound imaging probe is disclosed that provides non-invasive image acquisition in real-time without the use of ionizing radiation which could potentially harm the patient. In addition, it is cost effective, it typically provides good soft tissue contrast and it is often the diagnostic tool of choice for cardiology patients.

Structurally, various embodiments of the disclosure include multiplanar motion management system for non-invasive cardiac ablation comprising: a multiplanar imaging probe configured to acquire live multiplanar images within a probe volume, the multiplanar images being non-parallel; a probe localization system configured to acquire positional data of the multiplanar imaging probe; an input/output (I/O) management system configured to concurrently receive the live multiplanar images and the positional data, and to establish acquisition times for the multiplanar images and for the positional data; and a gating system configured to receive and process the live multiplanar images, the positional data, and the acquisition times. The gating system includes a processor that may be configured to: identify a cardiac phase corresponding to the live multiplanar images; define a set of reference coordinates from the positional data that closest corresponds in time to the live multiplanar images; and perform a rigid registration of the live multiplanar images to reference multiplanar images, the reference multiplanar images being representative of the cardiac phase. Some embodiments include a heartbeat sensing system for generating cardiac cycle data, wherein: the heartbeat sensing system is configured to generate a trigger signal based on the cardiac cycle data; the I/O management system is configured to receive the trigger signal concurrently with the multiplanar images and the positional data, and to generate trigger signal information that includes an acquisition time corresponding to the trigger signal; and the gating system is configured to receive and process the trigger signal information for identification of a start of a cardiac cycle. The gating system may be configured to utilize the trigger signal information to confirm the cardiac phase. In some embodiments, the heartbeat sensing system is an electrocardiogram (ECG) system and the cardiac cycle data is generated from an electrocardio signal. The positional data may be relative to a reference coordinate system, and the positional data may localize a location and orientation of the multiplanar imaging probe in three-dimensional space. The multiplanar imaging probe may be configured to acquire the multiplanar images simultaneously, and may include a geometry configured to mount on the thorax of a patient. In some embodiments, the multiplanar imaging probe acquires the multiplanar images at a rate that is in a range of 20 Hz to 50 Hz inclusive. In some embodiments, the multiplanar imaging probe is a multiplanar ultrasonic probe and the reference multiplanar images are ultrasonic images.

Various embodiments of the disclosure embody a method, comprising: (a) acquiring a series of reference multiplanar images of a beating heart within a patient with a multiplanar imaging probe; (b) during step (a), acquiring a reference position of the imaging probe for each of the reference multiplanar images of the reference series of multiplanar images; (c) identifying a cardiac phase for each reference multiplanar image of the reference series of multiplanar images; (d) acquiring a live multiplanar image with the multiplanar imaging probe during beam therapy treatment of the patient; (e) during step (d), acquiring a live position of the multiplanar imaging probe; (f) identifying a cardiac phase of the live multiplanar image; and (g) performing a rigid registration of the live multiplanar image and the live position to a corresponding reference image of the reference series of multiplanar images and a corresponding reference positions associated with the corresponding reference image, the corresponding reference image being representative of the cardiac phase of the live multiplanar image, the rigid registration providing a live heart position of the beating heart during the beam therapy treatment of the patient relative to a three-dimensional coordinate system to provide a live displacement of the beating heart between relative to the reference position.

In some embodiments, method includes a step of configuring a tangible, non-transitory medium the enumerated steps as instructions. The instructions in the step of configuring includes generating a status condition based on a comparison of the displacement with a predetermined threshold value. The method may also include affixing the multiplanar imaging probe to a thorax of the patient for use during execution of a reference simulation. In some embodiments, the method includes affixing the multiplanar imaging probe to a thorax of the patient for use during execution of a simulation stage. The method may include instructing the patient to breath hold over at least one cardiac cycle to effect the known respiratory state. The known respiratory state may be an end-expiration respiratory phase. The reference series of multiplanar images may be acquired at the start of a treatment process. In some embodiments, the reference series of multiplanar images is acquired during a simulation stage prior to a treatment stage.

In some embodiments, the method includes coupling a multiplanar imaging probe and a probe localization system to a gating controller, the gating controller including the set of instructions preconfigured on a non-transitory computer readable medium for execution in real time. The instructions of the gating controller may include generating a status condition based on a comparison of the displacement with a predetermined threshold value. In some embodiments, the method includes configuring the non-transitory computer readable medium with the instructions.

Various embodiments of the disclosure include a method for determining a position of cardiac structures in a known three-dimensional coordinate system, comprising: providing a multiplanar imaging probe and a localization system for tracking the multiplanar imaging probe in three-dimensional space; providing instructions on a tangible, non-transitory medium. The instructions may include: acquiring a first sequence of multiplanar images of a heart with the multiplanar imaging probe over a duration of multiple heartbeats while the patient is in a known respiratory state, the heart being at a first position; during the step of acquiring the first sequence, localizing the multiplanar imaging probe with the localization system to define a first set of reference coordinates at the first position; acquiring a second sequence of multiplanar images of the heart with the multiplanar imaging probe over a duration of multiple heartbeats while the patient is in the known respiratory state, the heart being at a second position; during the step of acquiring the second sequence, localizing the multiplanar imaging probe with the localization system to define a second set of reference coordinates at the second position; identifying a first set of representative multiplanar images from the first sequence of multiplanar images and a second set of representative multiplanar images from the second sequence of multiplanar images, the first set of representative multiplanar images and the second set of representative multiplanar images corresponding to a known combination of a cardiac motion phase and a respiratory motion phase; aligning the second set of reference coordinates with the first set of reference coordinates; and quantifying a translational displacement and a rotational displacement of the second set of representative multiplanar images relative to the first set of representative multiplanar images within the aligned first and second set of reference coordinates. In some embodiments, the known combination of cardiac motion phase and respiratory motion in the step of identifying correspond with an end-expiration of the respiratory motion phase. The instructions in the step of providing instructions may include displacing a patient support in accordance with the translational displacement and the rotational displacement. In some embodiments, the instructions in the step of providing instructions include instructing the patient to breath hold over at least one cardiac cycle during the step of acquiring the first sequence of multiplanar images to effect the known respiratory state. The step of acquiring the first sequence of multiplanar images of the instructions may be performed at an end-expiration respiratory phase to effect the known respiratory state.

Various embodiments of the disclosure include a method for inferring displacement of the heart resulting from respiratory motion from a multiplanar imaging probe mounted to a thorax of a patient, comprising: providing a multiplanar imaging probe; providing instructions on a tangible, non-transitory medium. The instructions comprise: acquiring a reference series of multiplanar images with the multiplanar imaging probe, the multiplanar imaging probe being affixed to a thorax of a patient; identifying a cardiac phase for each multiplanar image of the reference series of multiplanar images; acquiring a live multiplanar image with the multiplanar imaging probe during irradiation treatment of the patient, the multiplanar imaging probe being affixed to the thorax of the patient; identifying a cardiac phase for the live multiplanar image; and performing a rigid registration of the live multiplanar image to a corresponding image of the reference series of multiplanar images, the corresponding image of the reference series being representative of the cardiac phase of the live multiplanar image.

BRIEF DESCRIPTION OF THE DRAWINGS

FIG. 6 is a workflow diagram illustrating a treatment stage for delivering radiation therapy according to an embodiment of the disclosure;

FIGS. 7 through 9 illustrate the alignment of treatment stage images with simulation stage images according to an embodiment of the disclosure;

DETAILED DESCRIPTION

Figure 1:
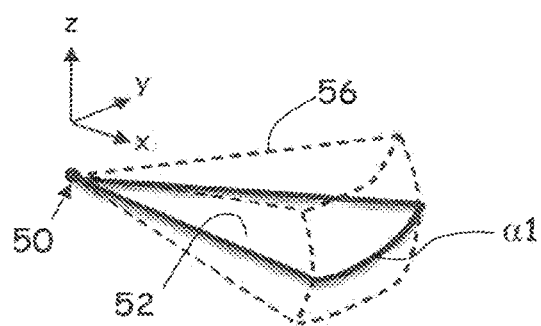
FIGS. 1 and 2 are perspective views of an ultrasound probe for acquiring multiplanar images in two non-parallel imaging planes according to an embodiment of the disclosure.
Figure 2:
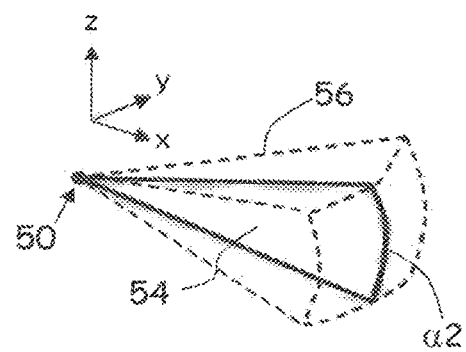
Figure 3:
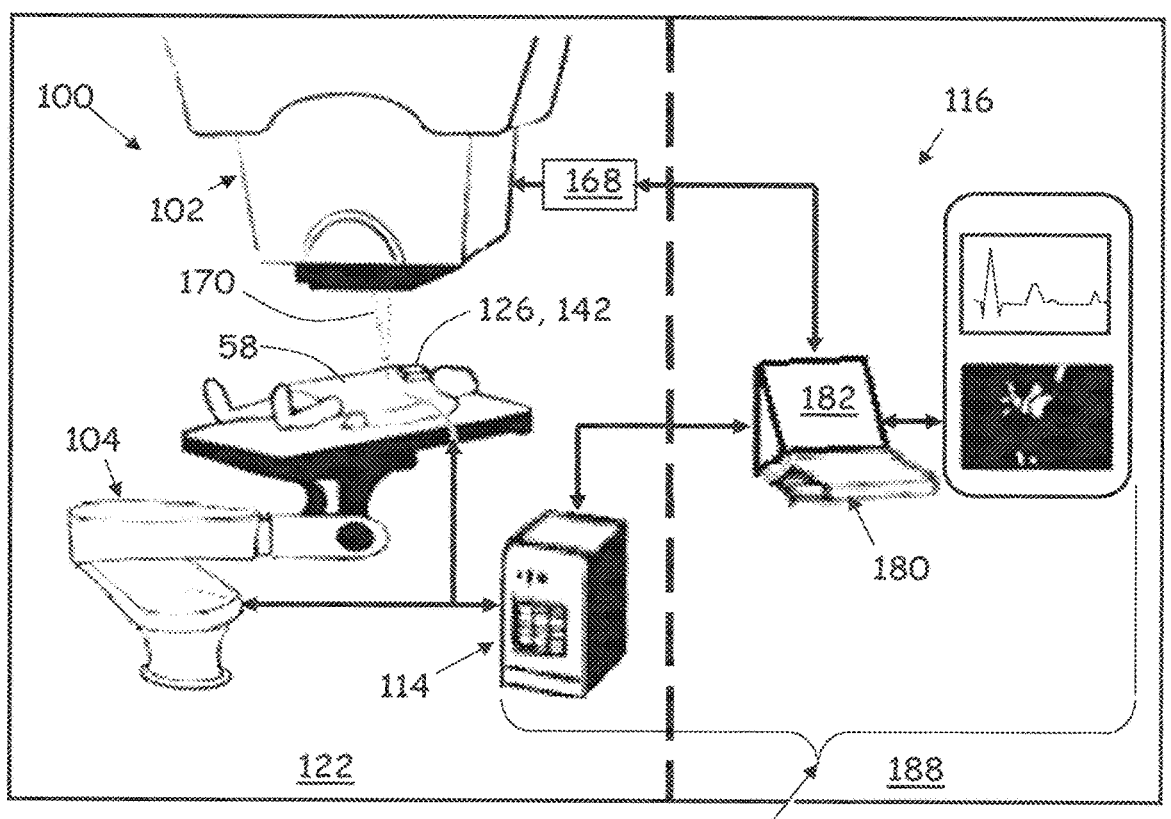
FIG. 3 is a simplified perspective view of a non-invasive cardiac ablation system system according to an embodiment of the disclosure.

Referring to FIGS. 1 and 2, the action of a multiplanar ultrasound probe 50 is depicted according to an embodiment of the disclosure. The multiplanar ultrasound probe 50 is configured to acquire images in two non-parallel imaging planes 52 and 54. In some embodiments, the non-parallel imaging planes 52 and 54 are orthogonal to each other, referred to arbitrarily as the x-y plane (FIG. 2) and the x-z plane (FIG. 3). The multiplanar ultrasound probe 50 includes a two-dimensional array of sensors (not depicted) that may be scanned to provide an effective probe volume 56. The multiplanar ultrasound probe 50 may image each of the multiplanar images with resolution characteristics similar to single two-dimensional ultrasound imaging. Such multiplanar ultrasound probes are commercially available, for example the XMATRIX® X5-1 or X7-2t array transducer, provided by Koninklijke Philips Electronics N.V. of Eindhoven, Netherlands.

Figure 4:
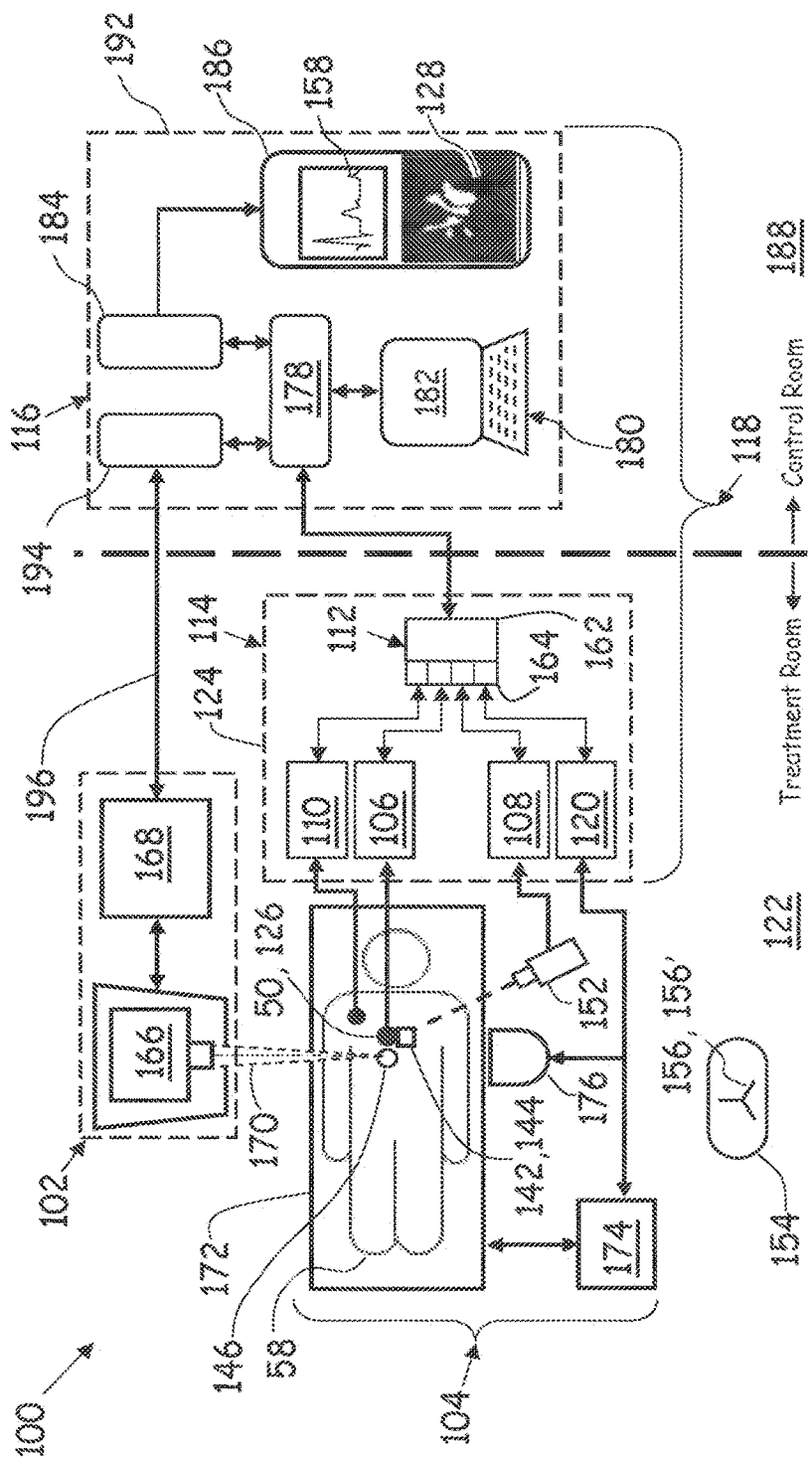
FIG. 4 is a schematic of the non-invasive cardiac ablation system of FIG. 3 according to an embodiment of the disclosure.

In some embodiments, the design of the probe is adapted to reduce the number of metallic components inside its casing, which reduces the appearance of artifacts on, for example, CT or cone beam CT imaging. The multiplanar ultrasound probe 50 may have a geometry (not depicted) which is tailored for positioning on the thorax of a patient 58 (FIG. 4). In some embodiments, the multiplanar images are acquired at an image refresh rate that is in a range of at least 10 to 30 Hertz inclusive. In some embodiments, the image refresh rate is in a range of 10 to 50 Hertz inclusive. In some embodiments, the image refresh rate is in a range of 10 to 100 Hertz inclusive. Herein, a range that is said to be "inclusive" includes the end point values of the stated range.

Functionally, the multiplanar ultrasound probe 50 enables live acquisition of non-parallel images (FIG. 4) simultaneously or in sequence, wherein "live" is defined as real time or near-real time acquisition sufficient for image monitoring. The non-parallel images acquired with the multiplanar ultrasound probe 50 enable monitoring of the heart motion in three-dimensional spatial coordinates within the effective probe 56. The non-parallel imaging planes 52 and 54 provide information in three dimensions about the imaged anatomical structures.

Referring to FIGS. 3 and 4, a non-invasive cardiac ablation system 100 is depicted according to an embodiment of the disclosure. The non-invasive cardiac ablation system 100 includes a therapy beam emitting system 102, a patient positioning system 104, a multiplanar imaging system 106, a probe localization system 108, and a heartbeat sensing system 110. The systems 106, 108, and 110 are controlled by a real time data acquisition system or DAQ 112, all of which are part of an input/output (I/O) management system 114. The I/O management system 114 interfaces with a beam gating system 116 to present a multiplanar motion management system 118. The I/O management system 114 may also include auxiliary interface(s) 120 for interfacing with other components of the non-invasive cardiac ablation system 100, for example the patient positioning system 104.

The I/O management system 114 concurrently acquires data sets from different data streams and establishes the time of acquisition ("time stamps") corresponding to each data set. In some embodiments, the I/O management system 114 includes components for the acquisition of three types of data: ultrasound data, electrocardiogram (ECG) data, and optical localization data. The I/O management system 114 may be physically located in a treatment room 122 and, in some embodiments, housed or based in an I/O cabinet 124.

The multiplanar imaging system 106 is coupled to a multiplanar imaging probe 126 (e.g., multiplanar ultrasound probe 50) for generation of non-parallel multiplanar images 128 in real time or near real time for visualization of the heart. The multiplanar imaging system 106 may include the multiplanar ultrasound probe 50, a probe holder 142, and a beam former (not depicted). The beam former generates timed electrical signals that sends the ultrasound wave into the patient, collects the electrical signals coming from the probe elements based on the reflection in the patient of the acoustics waves, and processes the incoming signals in order to generate an ultrasound image.

The multiplanar images 128 may resolve a target region 146 directly or otherwise enable inference of the position of the target region 146. The multiplanar imaging probe 50, 126 and/or probe holder 142 may include or be fitted with one or more localization markers 144. The multiplanar imaging system 106 may be configured to withstand some level of radiation exposure, such as indirect emission of neutrons, protons and gamma rays from the proximate particle beam. Alternatively, some components of the multiplanar imaging system 106 (e.g., data processor) can be remote and signals transmitted via analog or digital transmission cables.

Use of the multiplanar ultrasound probe 50 as the multiplanar imaging probe 126, prevalent throughout this disclosure, is non-limiting. The skilled artisan, in light of this disclosure, will recognize that the concepts disclosed herein are not limited to ultrasound imaging, but may incorporate other non-parallel imaging devices and techniques that may be incorporated mutatis mutandis. Other multiplanar imaging systems 106 and attendant multiplanar imaging probes 126 are contemplated for the non-invasive cardiac ablation system 100, for example x-rays, MRI, and ECGI systems.

The probe localization system 108 may be an optical system, for example, a camera 152 fixed to view the localization markers 144. In one embodiment, the camera 152 is an infrared (IR) camera, such as the FUSIONTRACK® 500 available from Atracsys, SARL of Puidoux, Switzerland, or the POLARIS VEGA® XT available from Northern Digital Inc. of Waterloo, Canada. This type of camera can localize infrared-reflective or LED markers in 6 degrees of freedom in three-dimensional space, for example in the form of positional data that establishes the location and rotational orientation of the marker relative to the camera 152. Alternatively, the probe localization system 108 may operate by other principles, including electrical, magnetic, or acoustic. The probe localization system 108 may also include surface tracking capabilities, for example using lasers or thermal imaging.

In some embodiments, the localization marker(s) 144 are positioned in a CT room (not depicted) during a simulation stage 200 (FIG. 5) and in the treatment room 122 during a treatment stage 300 (FIG. 6). The CT and treatment rooms may include a common room or reference coordinate system 154 for generating reference pixel coordinates 156', 156 relative to a treatment isocenter (not depicted) of the non-invasive cardiac ablation system 100, where reference pixel coordinates 156' refer to the simulation stage 200 and reference pixel coordinates 156 refer to the treatment stage 300. A calibration procedure with a dedicated calibration phantom (not depicted) may be used so that the probe localization system 108 provides a position and orientation of the multiplanar imaging probe 50, 126 in a congruent room coordinate system 154. Such calibration phantoms are known in the art, for example as used by Lachaine et al., "Intrafractional prostate motion management with the Clarity Autoscan system," Medical physics international, 1 (2013).

The heartbeat sensing system 110 generates cardiac cycle data 158, such as an ECG measuring the electrical activity generated by the heart. The heartbeat sensing system 110 monitors heartbeat signal acquisition and outputs a trigger signal that is received by the I/O management system 114. In some embodiments, the I/O management system is configured to receive the trigger signal concurrently with the multiplanar images 128. For ECG systems, both amplitude and R-peak triggers of an electrocario signal may be monitored. An ECG system outputs the trigger pulse upon detection of the R-peak, the trigger pulse being received and time stamped by the I/O cabinet. The ECG system may also control the switching between ECC leads.

The DAQ 112, which controls at least the systems 106, 108, and 110, may include a programmable logic controller (PLC) 162 and various I/O modules 164. The PLC 162 and I/O modules 164 execute the start and stop triggering as well as the accurate time-stamping of the imaging, heartbeat, and localization data streams.

The therapy beam emitting system 102 and patient positioning system 104 are optionally coupled to the I/O management system 114. The therapy beam emitting system 102 may include a particle emitter 166 and a beam controller 168 for selectively generating a particle beam 170 which is delivered to the target region 146. The patient positioning system 104 may include a patient support 172 and a positioner system 174. In some embodiments, the non-invasive cardiac ablation system 100 includes a patient position verification system 176 which may also be coupled to the I/O management system 114. The patient position verification system 176 may include a double X-ray or a cone-beam computed tomography (CBCT) imaging system for verification of the patient positioning. Additional details of the therapy beam emitting system 102, patient positioning system 104, and the patient position verification system 176 are available at Garonna et al.

The beam gating system 116 includes hardware control and signal capabilities that are coupled to a gating controller 178. The target motion management system 118 may include a control console 180 for user interface with the gating controller 178. The control console may include a graphical user interface (GUI) 182 to facilitate user input and information display. The gating controller 178 is operatively coupled to receive input from and/or send output to the therapy beam emitting system 102, the patient positioning system 104, the multiplanar imaging system 106. The gating controller 178 may be interfaced with the I/O management system 114 via the DAQ 112. In addition to controlling and coordinating the hardware components of the non-invasive cardiac ablation system 100, the gating controller may include computer memory for storage and execution of the various computational tasks required of the beam gating system 116, including but not limited to registration of multiplanar images, determination of cardiac phase (e.g., pursuant to Garonna et al.).

The beam gating system 116 processes the data and generates updated information to the user and to the non-invasive cardiac ablation system 100. The beam gating system 116 may be used for real time or near real time processing of the image, heartbeat, and localization data streams, for example, using a graphics processing unit (GPU) 184. Alternatively, the GPU 184 may be located in the treatment room 122 and housed in the I/O cabinet 124 as part of the I/O management system 114. The GPU 184 may be in communication with the GUI 182 and auxiliary display monitors 186 that, for example, display data such as the multiplanar images 128 and the cardiac cycle data 158. The beam gating system 116 may also receive information from the operator through the GUI 184. The beam gating system 116 may be remotely located in a control room 188 separate from the treatment room 122 and, in some embodiments, is housed or based on a workstation platform 192.

The beam gating system 116 may also include an interface 194 that communicates with the beam controller 168 via a communication channel 196. The communication channel 196 may be an analog or digital cable, or a wireless channel. The beam gating system 116 sends a gating signal via the communication channel 192 to enable or gate the particle emitter 166. Herein, to "enable" the therapy beam emitting system 102 is to cause the particle beam 170 to irradiate the patient 58, while to "gate" the therapy beam emitting system 102 is to prevent the particle beam 170 from irradiating the patient 58. More generally, the term "beam-gating" refers to sending a signal to the beam controller 168 to either pause or resume delivery of the therapy beam 170 as planned. The way such enablement and gating is achieved is system specific. Some systems enable the particle beam 170 by activating an accelerator of the therapy beam emitting system 102 and gate the particle beam 170 by deactivating the accelerator. Other systems leave the accelerator activated and gate the particle emitter 166 by blocking or diverting the particle beam 170 so that the patient 58 is not irradiated.

Functionally, the probe localization system 108 enables tracking of the multiplanar imaging probe 50, 126 in three-dimensional space in order to associate the localization markers 144 with anatomical structures in the multiplanar image 128. The probe localization system 108 enables localization and continuous monitoring of the position localization markers 144 in the room coordinate system 154.

The probe localization system 108 can be used to monitor respiratory motion. The multiplanar imaging probe 50, 126 and/or probe holder 142, being equipped with the localization marker(s) 144 and arranged on the thorax for imaging of the heart, is suitably positioned to follow tidal motion of respiration. As such, the localization marker(s) 144 may act as an external surrogate for respiratory motion. The probe localization system 108 can thereby provide external information about respiratory motion proximate the heart and the target region 146.

In operation, the multiplanar motion management system 118 may be used during the simulation stage 200 (FIG. 5) prior to the treatment delivery and/or during the treatment stage 300 (FIG. 6) where treatment delivery is executed. The multiplanar imaging probe 50, 126 may be secured to the patient 58 with a probe holder 142, for example on the thorax of the patient 58 for an apical or parasternal viewing window. The multiplanar imaging probe 50, 126 is immobilized on the thorax of the patient 58 using the probe holder 142, enabling hands free operation. In some embodiments, signal processing of the beam former of the multiplanar ultrasound probe 50 is utilized to reconstruct an image for visualization.

The multiplanar imaging system 106 may provide continuous visualization of the heart trans-abdominally (through the diaphragm or the liver) or trans-thoracically (between the ribs). The multiplanar imaging probe 50, 126 may be non-parallel, placed in apical position or parasternal position, and/or image long-axis or short-axis heart structures affected by heart motion.

The non-invasive cardiac ablation system 100 also delivers the particle beam 170 to the target region 146 at predetermined phases of certain bodily motion cycles. Such bodily motion cycles may include respiratory and cardiac cycles. The multiplanar imaging system 106 provides the multiplanar images 128 from the real-time imaging to the target motion management system 118. The target motion management system 118 utilizes the multiplanar images 128 to deliver the particle beam 170 at the predetermined respiratory and cardiac phases, for example as described by Garonna et al. The multiplanar images 128 may also include information regarding the properties required of the particle beam 170, which may also be determined by the gating controller 178.

The multiplanar images 128 and cardiac cycle data 158 may be acquired and updated to the target motion management system 118 continuously, providing the operator with a live stream of information. The multiplanar images 128 and cardiac cycle data 158 may also be stored on a storage medium and later analyzed to assess the accuracy of the phase prediction process and, if needed, to adapt the software parameters specific to the patient 58.

Figure 5:
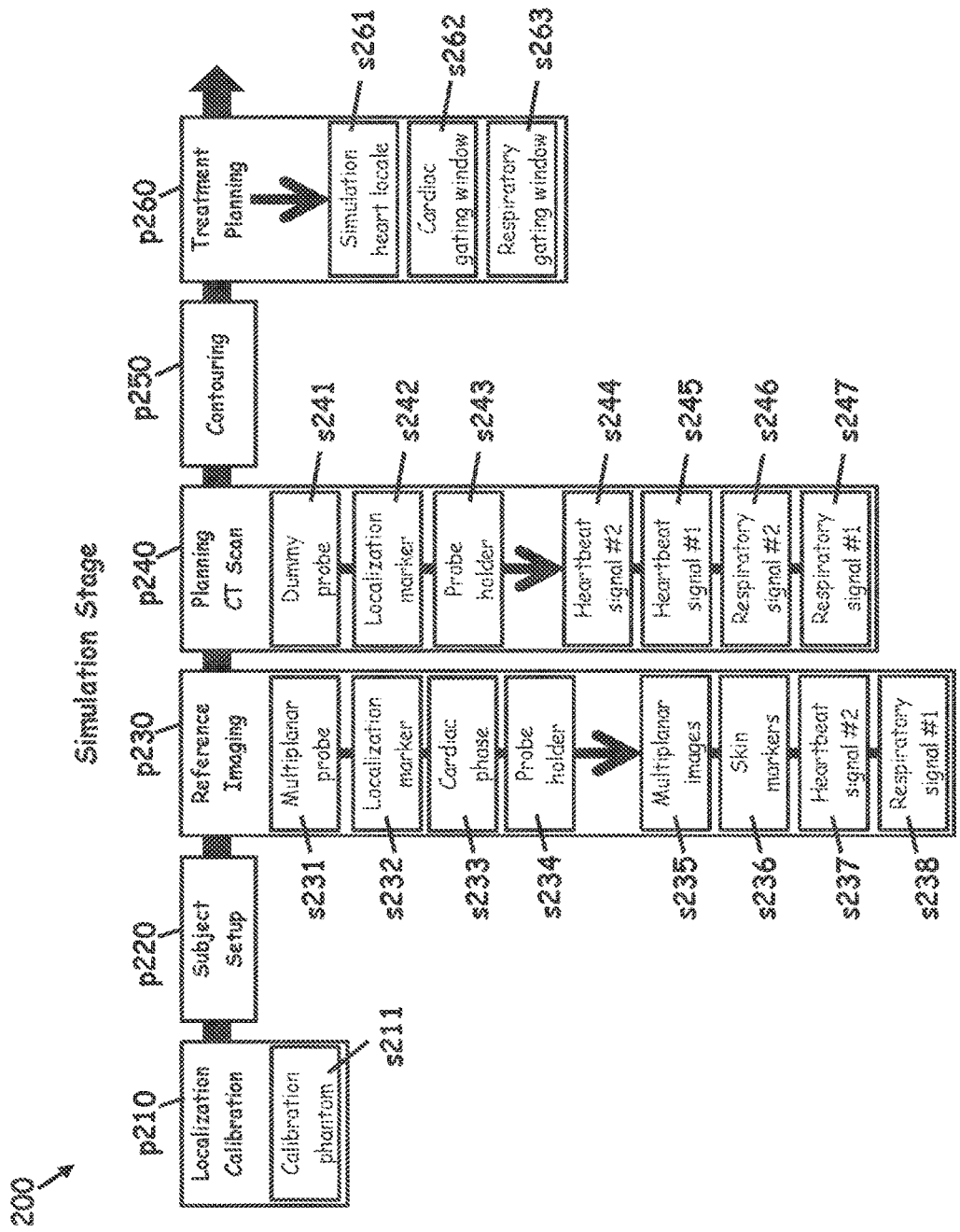
FIG. 5 is a workflow diagram illustrating a simulation stage for development of a treatment plan according to an embodiment of the disclosure.

Referring to FIG. 5, workflow for a simulation stage 200 is diagrammed according to an embodiment of the disclosure. During the simulation stage 200, all data and anatomical information (e.g., medical images) required for treatment planning are gathered, from which a patient-specific treatment plan is developed. The simulation stage 200 may include a series of processes, each process being designated in FIG. 5 by a reference character beginning with the letter "p". The processes of the simulation stage 200 may include: a localization system calibration process (p210) which, in some cases, need only be performed intermittently; a subject setup process (p220); a reference imaging process (p230); a planning CT scan process (p240), a contouring process (p250); and a treatment planning process (p260). Various of the processes are depicted as including one or more steps, designated in FIG. 5 by a reference character beginning with the letter "s".

In some embodiments, the localization calibration process (p210) of the simulation stage 200 takes place in the CT imaging room and includes calibration of the probe localization system 108 using a specifically designed calibration phantom (s211). The calibration phantom step (s211) enables the multiplanar imaging probe 50, 126 to be localized in the room coordinate system 154 (e.g. of the CT imaging room) at later processes and stages. A patient or subject setup process (p220) is executed, wherein the patient 58 is positioned on the CT table following a standard oncological radiotherapy procedure. The subject setup process (p220) may include the use of standard immobilization and patient support devices.

A reference imaging process (p230) is performed, wherein reference multiplanar images are acquired with the multiplanar imaging probe 50, 126 (s231) fixed to the thorax of the patient using the probe holder 142 (s234). During image acquisition, the multiplanar imaging probe 50, 126 may be localized by the probe localization system 108 using the localization markers 144 (s232). In this way, a position of the multiplanar imaging probe 50,126 (referred to herein as the "reference position") during the acquisition of each reference multiplanar image can be determined with respect to the room coordinate system 154 (s235). The cardiac phase is determined for each of the reference multiplanar images acquired in the reference imaging process p230 (s233). During the acquisition of the reference multiplanar images, skin markers may be placed on the skin of the patient 58 (s236) to aid in repositioning of the multiplanar imaging probe 50, 126 at the treatment stage 300 (FIG. 6). In some embodiments, cardiac cycle data 158 is acquired during the simulation stage (s237). Additionally, the time-resolved position of the localization markers 144 may be used as a respiratory signal (s238).

In some embodiments, the planning CT scan process (p240), the contouring process (p250), and the treatment planning process (p260) of the simulation stage 200 may implement standard oncological radiotherapy procedures. The planning CT scan process (p240) may include planning four-dimensional (three spatial dimensions plus time) computer tomography (4D-CT) scan acquisitions. In some embodiments, a dummy probe is utilized during the acquisition of the planning CT acquisition (s241) to avoid undesirable artifacts on the CT scan generated by metallic parts of the multiplanar imaging probe. The dummy probe may also be localized by the probe localization system 108 using localization markers (s242). Additional cardiac cycle and respiratory data may also be acquired (s244-s247). The 4D-CT scans may be both respiratory- and cardiac-gated. During the contouring process (p250), the radiation target is contoured and, in general, organs at risk near the target region 146 are also contoured. An example relevant contouring process is found at Blanck et al., "Radiosurgery for ventricular tachycardia: preclinical and clinical evidence and study design for a German multi-center multi-platform feasibility trial (RAVENTA)," *Clin Res Cardiol* 109, 1319-1332 (2020).

In some embodiments, two heartbeat signals are acquired during the planning CT scan process (p240). The planning CT scan is reconstructed using data from a heartbeat signal #1 (s244) which is typically acquired by a first heartbeat sensing system that is connected directly to the CT scanner. Treatment delivery is based on a heartbeat signal #2 (s245) which is acquired the heartbeat sensing system 110 of the I/O management system 114. For ECG systems, the start of a cardiac cycle is usually identified using R-peak information, but different ECG suppliers typically have their own way of identifying the R-peak (e.g., just after or just before the actual peak). Accordingly, the disclosed embodiment includes provisions for acquiring signals from both heartbeat sensing systems simultaneously, to establish a correlation between the R-peak identification of the respective heartbeat sensing systems. Alternatively, the CT scanner may utilize heartbeat signal #2 from the heartbeat sensing system 110 instead of its own heartbeat signal #1, or the I/O management system 114 may utilize heartbeat signal #1 from the CT scanner instead of its own heartbeat signal #2, thereby eliminating the need for correlation.

Likewise, in some embodiments, two respiratory signals RESP #1 and RESP #2 may be acquired during the planning CT scan process (p240). The planning CT scan is reconstructed using data from RESP #1 (s247) which may be acquired by a first localization system available in the CT imaging room (or any other respiration motion surrogate signal). Treatment delivery is based on RESP #2 (s246) which may be acquired by the probe localization system 108 of the I/O management system 114. Each localization system may have peculiarities that require correlation. For example, where localization is performed with optical tracking systems, aspects of one optical tracking system may differ from that of the other optical tracking system. Such aspects include the position of the optical tracking system with respect to the tracked object, the acquisition rate, the acquisition latency. Accordingly, the disclosed embodiment includes acquiring signals from both localization systems simultaneously, to establish a correlation between the respiratory motion as detected by respective localization systems.

Alternatively, the CT imaging room may utilize RESP #2 from the probe localization system 108 instead of its own RESP #1, or the I/O management system 114 may utilize RESP #1 from the localization system used in the CT imaging room instead of its own RESP #1, eliminating the need for correlation.

In some embodiments, the treatment planning process (p260) includes determining three input characteristics for the treatment stage 300: (1) a desired location of the treatment isocenter (s261) in the coordinates provided by the room coordinate system 154; (2) a cardiac gating window (s262), given by the treatment plan and determining when the radiation beam should be enabled or disabled based on the heart motion; and (3) a respiratory gating window (s263), given by the treatment plan and determining when the radiation beam should be enabled or disabled based on the respiratory motion. Additionally, the treatment planning process generates the contours for the target and all relevant organs for at least one reference CT.

Referring to FIG. 6, a workflow for a treatment stage 300 is diagrammed according to an embodiment of the disclosure. The treatment stage 300 facilitates delivery of radiation doses accurately to the target while sparing the surrounding normal tissues as much as possible. The treatment stage 300 includes a series of processes, each process being designated in FIG. 6 by a reference character beginning with the letter "p". The processes may include: a localization system calibration process (p310) which, in some cases, need only be performed intermittently; a subject setup process (p320); a multiplanar probe setup process (p330); a bone alignment process (p340); a heart alignment process (p350); a start treatment process (p360); and a gating process (p370). Various of the processes are depicted as including one or more steps, designated in FIG. 6 by a reference character beginning with the letter "s".

In some embodiments, the treatment stage 300 starts with the calibration of the probe localization system 108 (p310), again using the calibration phantom (s311). During the subject setup process (p320), the patient 58 is positioned on the table in the same way as in the simulation stage 200. In some embodiments, an initial alignment of skin marks with the treatment room isocenter is performed during the subject setup process (p320), for example, with a laser system available in the treatment room, or with surface imaging systems. The multiplanar imaging probe 50, 126 is positioned and immobilized on the thorax of the patient 58 with the probe holder 142 (s333). To assist with positioning of the multiplanar imaging probe 50, 126 at the same position on the patient 58 as during the simulation stage, skin marks as well as information from the localization markers (s332) may be utilized.

With the multiplanar imaging probe 50, 126 in a fixed position, the patient 58 is aligned using the room coordinate system 154. In some embodiments, the bone alignment process (p340) includes an alignment of the patient 58 based on the bony anatomy, for example using cone-beam CT (s341). During the table alignment step (s342), misalignment is computed based on comparison of bony anatomy from the simulation stage 200 and the treatment stage 300, as identified, for example, with CT, CBCT, or X-ray images. The misalignment is corrected by manipulation of the patient support 172 using the patient positioner 174 to bring the patient 58 into alignment with the simulation orientation. In some embodiments, the correction is performed using the multiplanar motion management system 118 via one of the auxiliary interfaces 120 to control the patient positioning system 104.

During the heart alignment process (p350), live multiplanar images are acquired and registered to the reference multiplanar images that were acquired during the simulation stage 200 (at s235 of p230 of FIG. 5). This rigid registration (s351) is referred to generally as a "live-to-simulation" image registration, and occurs between images of the same data type. For example, when using the multiplanar ultrasound probe 50, the live and simulation images are both ultrasound images, and may be referred to as an "ultrasound-to-ultrasound" or "US-to-US" image registration. The process applies generally regardless of whether the multiplanar images 128 are ultrasound images. In some embodiments, the ultrasound-to-ultrasound image registration serves as a final verification of the patient setup. For the table fine tuning step (s353), misalignment is computed based on comparison of soft tissue contrast of the heart from the simulation stage 200 and the treatment stage 300, as identified with the multiplanar images 128. The necessary translations and rotations to correct the misalignment are performed with the positioner system 174, optionally using the multiplanar motion management system 118.

At the start of the treatment and gating processes (p360 and p370), live multiplanar images are continuously acquired and processed in real time or near real time (s371), with the probe localization system 108 simultaneously tracking the multiplanar imaging probe 50, 126 (s372). The cardiac phase is determined live for each of the reference multiplanar images acquired in the reference imaging process p230 (s233). Based on the live multiplanar images, four different outputs are generated: (1) heart displacement information for drift monitoring (s374); (2) a respiratory gating signal (s375); (3) a cardiac gating signal (s376) (e.g., such as disclosed in Garonna et al.); and (4) associated warnings and interlocks (s377), such as patient physiological changes that may require medical attention and patient physiological changes that require treatment interruption.

Referring to FIGS. 7 through 9, a patient setup method 400 that enhances alignment of the patient to the correct position in the room coordinate system 154 is depicted according to an embodiment of the disclosure. The patient setup method assists in setting up the patient 58 in the same position and orientation in the treatment stage 300 as in the simulation stage 200 by complementing the bony alignment setup with the heart alignment setup using multiplanar imaging. The patient setup method 400 may be accomplished during the heart alignment process (p350) of the treatment stage 300. Aspects of the method are outlined below.

At the simulation stage 200, during localization of the multiplanar imaging probe 50, 126 (FIG. 5), a simulation stage image sequence SIM is acquired over a duration of one or more heartbeats and one or more respiration cycles. Similarly, at the treatment stage 300, during localization of the multiplanar imaging probe 50, 126 (FIG. 6), a treatment stage image sequence TX is acquired over a duration of one or more heartbeats and respiration cycles.

From both the SIM and the TX sequences, the multiplanar images 128 belonging to a particular combination of cardiac and respiration motion phases are extracted (step 400a at FIG. 7), and the simulation stage reference pixel coordinates 156' and treatment stage reference pixel coordinates 156 are defined. For example, the images that correlate with an end-expiration respiratory phase and an end-systole cardiac phase could be extracted from each sequence. In this way, the cardiac and respiratory motion are in a same physiological state for the extracted images from the SIM and TX sequences. Determination of the known respiratory state may be performed by the gating controller. Such known respiratory state includes but is not limited to a breath hold condition or an end-expiration condition. Also, determination of the end-systole cardiac phase or other preferred cardiac phase may be determined by the gating controller.

A coarse rigid registration is performed at step 400*b* (FIG. 8). The coarse rigid registration overlaps images 402 and 402' from the SIM and TX sequences. The coarse rigid registration is based on the position of the effective probe volume 56 at the time of image acquisition (step 400*b* at FIG. 8). The coarse rigid registration 400*b* is performed without regard to the content of the SIM and TX images 402 and 402'.

A fine rigid registration is also performed, based on the content of the SIM and TX images 402 and 402' (step 400*c* at FIG. 9). The combination of the coarse and the fine registrations quantifies the translational and rotational displacement of the heart at treatment stage 300 relative to the simulation stage 200. Accordingly, the patient setup method (processes p320, p340, and p350 of the treatment stage 300 of FIG. 6) may provide translational and rotational instructions to the patient positioning system 104 for displacing the patient support 172 of the non-invasive cardiac ablation system 100 upon which the patient 58 is positioned, in order to correctly align the heart of the patient 58 with respect to the simulation stage setup (steps s342 and S353 of FIG. 6). The basic principles of coarse and fine rigid registration are disclosed by Khalil et al., "An Overview on Image Registration Techniques for Cardiac Diagnosis and Treatment," Cardiology research and practice, 2018 (2018), and by Che et al., "Ultrasound registration: A review," Methods, 115, 128-143 (2017).

The technique described above can also be used to monitor the heart displacement or "drift" in reference pixel coordinates 156 during the treatment stage 300. That is, the heart drift may also be measured with respect to the SIM images 402. The information can be visualized on the GUI 182 to enable interruption the treatment as the operator may deem necessary. In some embodiments, based on the inputs given by the operator prior to treatment delivery, the non-invasive cardiac ablation system 100 can automatically trigger warnings and/or interlocks and interrupt the particle beam 170 if, for example, the heart moves outside of the planned target margin (accounting for motion uncertainties) for too long.

In some embodiments, external and internal information is combined to monitor the motion of the heart due to respiration. Placement of the multiplanar imaging probe 50, 126 and attendant localization marker(s) 144 on the thorax of the patient (s332, s333 of FIG. 6) provides the external information, as discussed above. The multiplanar images 128 provides the internal information about the motion of the heart resulting from respiration. In fact, the multiplanar images 128 contain information about the motion of the heart as well as the motion of the multiplanar imaging probe 50, 126 in the reference pixel coordinates 156.

A combination of both the external and the internal information provides an accurate representation of the heart motion, whereas relying on external information enables only an inaccurate inference of the heart motion based on the movement of the surrounding anatomical structures, such as the lungs. The combination of internal and external information for respiratory motion management is an improvement over conventional systems and techniques, which are often limited to external information provided by an external surrogate.

Figure 10:
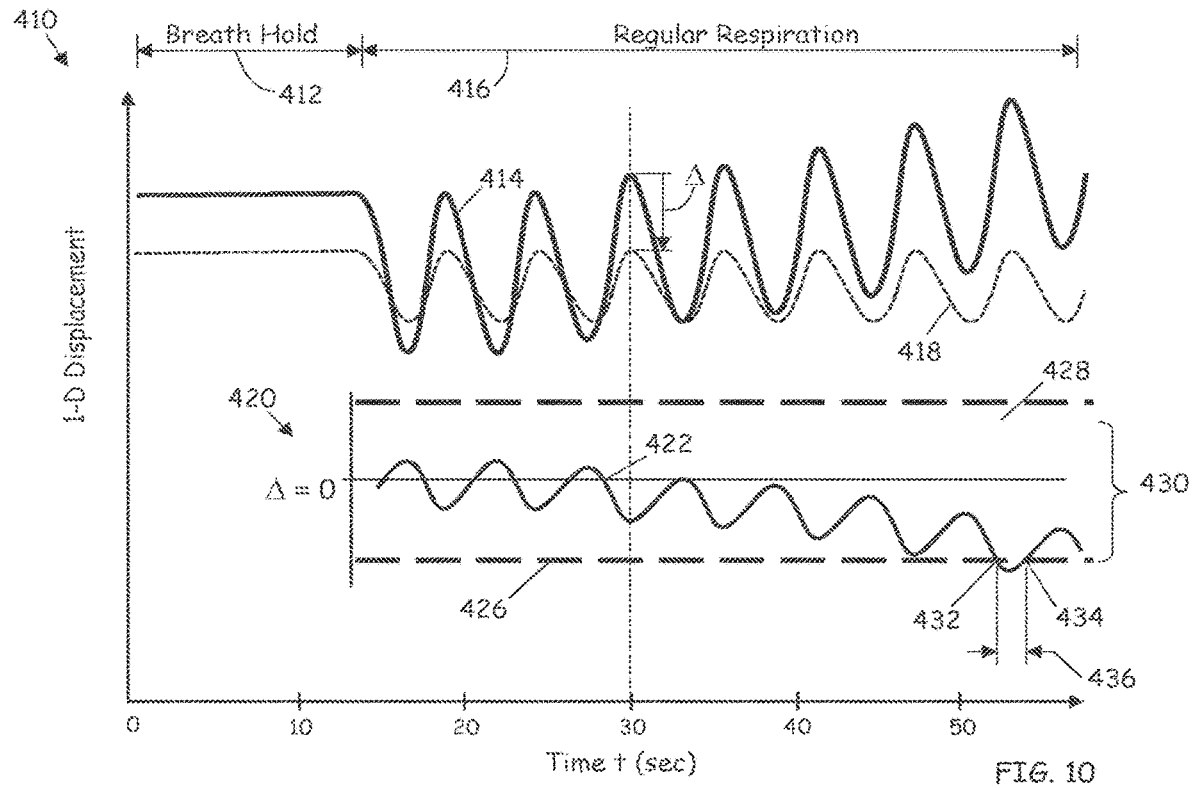
FIG. 10 is a plot depicting live-to-simulation registration and localization characteristics of heart displacement for analysis of respiratory cycle and heart drift according to an embodiment of the disclosure.

Referring to FIG. 10, various aspects of respiratory motion information are discussed according to an embodiment of the disclosure. The multiplanar images 128 inherently capture both the displacement of the heart relative to the multiplanar imaging probe 50, 126 (resulting from an anatomical structure displacement inside the thorax) and the displacement of the multiplanar imaging probe 50, 126 itself (resulting from thorax expansion and contraction). These combined displacements can be isolated and extracted from the multiplanar images 128 by a rigid registration process. The probe localization enables dissociation of the two contributions. The registration process enables determination of the heart displacement.

In some embodiments, at the start of the treatment (e.g., during the start treatment process p360 of FIG. 6), a series of reference multiplanar images of the beating heart of the patient are acquired when the patient is in a known respiratory state. The patient may be asked, for example, to hold his or her breath over one or more cardiac cycles, as depicted in a breath hold condition 412. For each reference multiplanar image in this breath hold or reference sequence 412, motion due to respiration is absent and the cyclical motion attributed to cardiac motion may be extracted in terms of cardiac phase based on the cardiac cycle data 158 or as described in Garonna et al. Alternatively, instead of generating the reference multiplanar images at the start of the treatment, the SIM images 402 generated during the simulation stage 200 (acquired at s235 of p230 of FIG. 5) may be used.

During the treatment stage 300, a series of live multiplanar images is acquired. A rigid registration of each live multiplanar image to a reference multiplanar image of corresponding cardiac phase is performed. For example, if the cardiac phase for a given live multiplanar image is identified as being 0.3, that live multiplanar image is registered to a reference multiplanar image that corresponds to or represents the same cardiac phase of 0.3. This rigid (live-to-simulation) image registration may be similar to the steps for the TX to SIM registration described attendant to FIGS. 7 through 9 and include a fine and a coarse registration.

During treatment, the patient is able to breathe normally, as indicated by a fine rigid registration time trace 414 during a regular respiration condition 416. The fine registration time trace 414 of the live-to-simulation images depicts the displacement of the heart with respect to the probe because the images by themselves provide no indication of the spatial position of the probe volume 56 during the acquisitions. A localization marker time trace 418 presenting the displacement of the localization markers 144 during the regular respiration condition 416 is also presented in FIG. 10. In contrast, the localization marker time trace 418 provides only an indication of the displacement in position of the probe volume with respect to the room coordinates. The live multiplanar images acquired during regular respiration 416 are registered to the reference multiplanar image of corresponding cardiac phase. Because of the cardiac phase correlation of the reference and live multiplanar images, any relative displacement due to cardiac activity is effectively cancelled by the rigid registration, such that any displacement indication after the rigid registration of the live-to-simulation (ultrasound-to-ultrasound) images is due primarily to respiratory motion and/or heart drift relative to the multiplanar imaging probe 50, 126. The motion of the heart due to respiration can thus be inferred from the difference between the rigid registration and localization time traces 414 and 418.

Inference of the heart motion due to respiration is accomplished by a full (coarse and fine) registration, also illustrated in FIG. 10. The procedure for the full registration is as follows: A difference Δ between the fine rigid registration time trace 414 and localization (coarse registration) time trace 418 is illustrated at a time t of 30 seconds in graph 410. The difference Δ may be in reference to the registration time trace 414, in which case the value of Δ illustrated at t=30 seconds is negative or inverted (represented by the down arrow in graph 410). A subplot 420 presenting a difference time trace 422 of differences Δ as a function of time is also provided in FIG. 10. The cyclical aspect of the difference time trace 422 represents the motion of the heart due to respiration, and provides a reliable and dynamic indication of the respiratory cycle for purposes of respiratory gating or motion monitoring.

Detection of heart drift is also depicted in subplot 420. Generally, the upward migration of the fine registration time trace 414 relative to the localization time trace 418 in graph 410 is indicative of heart drift. The heart drift is indicated in subplot 420 by a downward migration of the difference time trace 422. The opposite directions of the migration of time traces 414 and 422 is attributed to the inverted magnitude of the difference Δ. Over the initial respiratory cycle(s) of the regular respiration phase 416, a median datum line 424 may be established that represents the difference Δ of zero. An operating band 430 is bounded by lower and upper threshold values 426 and 428 of the difference Δ on the subplot 420. The operating band represents an allowable range of differences Δ within which the non-invasive cardiac ablation system 100 may operate. The difference time trace 422 is depicted as exceeding the operating band 430 at the lower threshold value 426 at an egress point 432 and returning to within the operating band 430 at a reentrance point 434. As such, there is a breach 436 of the operating band 430 that exists between the egress and reentrance points 432 and 434.

In some embodiments, the beam gating system 116 is configured to gate or disable delivery of the therapy beam 170 if the difference Δ is outside the operating band 430. The beam gating system 116 may also be configured to enable delivery of the therapy beam 170 if the difference Δ reenters the operating band 430. In some embodiments, the beam gating system 116 is configured to gate delivery of the therapy beam 170 only if the breach 436 exceeds a predetermined time duration. Likewise, the beam gating system 116 is configured to enable delivery of the therapy beam 170 only if the reentry into the operating band exceeds a predetermined time duration. In some embodiments, the upper and lower threshold values 426 and 428 is entered by the system operator, for example using the control console 180.

The graph 410 of FIG. 10 is included for purposes of illustration and presents one-dimensional displacement data along a single coordinate. The skilled artisan will recognize, in view of this disclosure, that the multiplanar imaging probe 50, 126 provides information in three dimensions, and therefore can provide displacement information in three dimensions.

The time traces 414 and 418 have the same temporal pattern, as both are a consequence of the patient respiration. As such, the localization marker time trace 418 may provide a redundancy that serves as a check to the live-to-simulation image registrations. Also, in case the live-to-simulation (e.g., US-to-US) registration fails, monitoring the localization marker(s) 144 localization can provide a backup for determining respiratory phase. In addition, the information provided by the localization marker may provide extra information which can be used to further understand how the anatomical structures around the heart are positioned.

Figure 11:
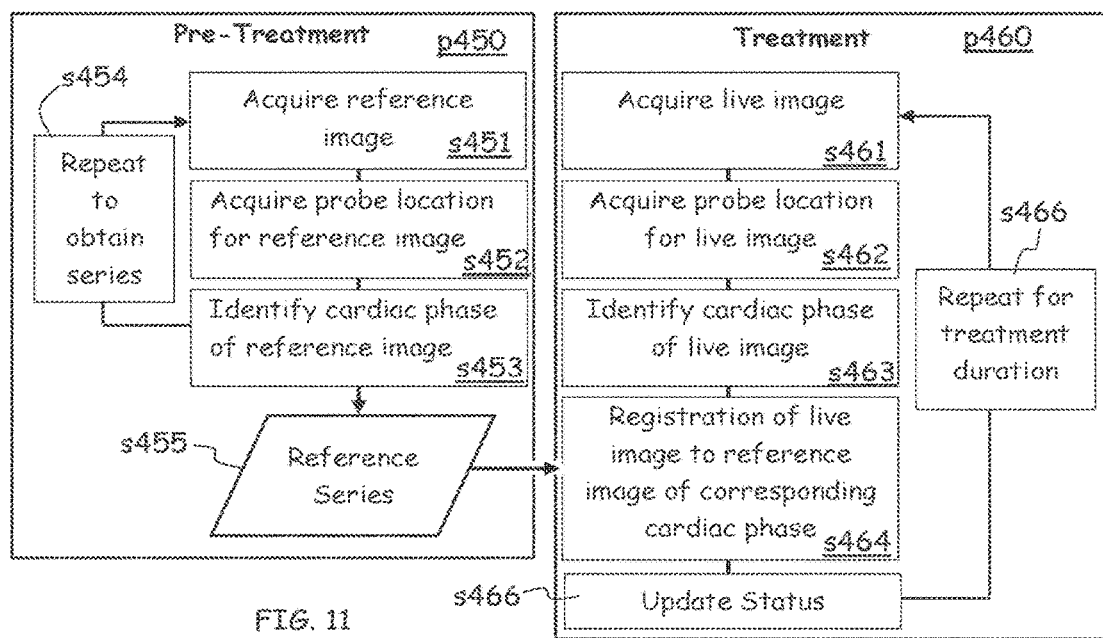
FIG. 11 is a flow chart of a method for extracting respiratory cycle and heart drift information of FIG. 10 according to an embodiment of the disclosure.

Referring to FIG. 11, a method for extracting respiratory motion information from the multiplanar images 128 based on the aspects of respiratory motion discussed at FIG. 10 is depicted according to an embodiment of the disclosure. A reference multiplanar image of a beating heart within a patient is acquired with a multiplanar imaging probe (s451); concurrently acquiring a reference position of the imaging probe for the reference multiplanar image of step s451 (s452); identifying a cardiac phase for the reference multiplanar image of step s451 (s453); and repeating steps s451 through s453 to acquire a series of reference multiplanar images and the corresponding probe locations and cardiac phases (s454). The series of reference multiplanar images is stored for access during the treatment process p460, for example in the computer-readable storage medium of the gating controller 178.

The treatment process 460 is subsequently executed: acquiring a live multiplanar image with the multiplanar imaging probe during beam therapy treatment of the patient (s466); concurrently acquiring a live position of the multiplanar imaging probe (s467); identifying a cardiac phase of the live multiplanar image (s467); performing a rigid registration of the live multiplanar image and the live position to a corresponding reference image of the reference series and a corresponding reference position associated with the corresponding reference image acquired at step s455, the corresponding reference image being representative of the cardiac phase of the live multiplanar image. The rigid registration provides a live heart position of the beating heart during the beam therapy treatment of the patient relative to a three-dimensional coordinate system to provide a live displacement of the beating heart relative to the reference position. In some embodiments, a status condition based on a comparison of said displacement with a predetermined threshold value is generated for updating by the beam gating system 116. Steps s461 through 466 are repeated for the duration of the external beam therapy treatment.

In some embodiments, steps of the various methods disclosed herein are provided in the form of instructions provided on a tangible, non-transitory medium, such as on a printed document, compact disc, or flash drive. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions may be complete on a single medium, or divided among two or more media. For example, some of the instructions may be written on a paper document that instruct the user to access one or more of the steps of the method over the internet, the internet-accessible steps being stored on a computer-readable medium or media.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

The following documents are hereby incorporated by reference herein in their entirety: Topolnjak et al., "Image-guided radiotherapy for left-sided breast cancer patients: geometrical uncertainty of the heart," International Journal of Radiation Oncology* Biology* Physics, 82(4), e647-e655 (2012); Kincaid Jr, et al., "Investigation of gated cone-beam CT to reduce respiratory motion blurring," Medical physics, 40(4), 041717 (2013); Nankali et al., "Geometric and dosimetric comparison of four intrafraction motion adaptation strategies for stereotactic liver radiotherapy," Physics in Medicine & Biology, 63(14), 145010 (2018); Fayad et al., "Correlation of respiratory motion between external patient surface and internal anatomical landmarks," Medical physics, 38(6Part1), 3157-3164 (2011); Robinson et al., "An evaluation of the Clarity 3D ultrasound system for prostate localization," Journal of applied clinical medical physics, 13(4), 100-112 (2012); De Luca et al., "The 2014 liver ultrasound tracking benchmark," Physics in Medicine & Biology, 60(14), 5571 (2015); Lachaine et al., "Intrafractional prostate motion management with the Clarity Autoscan system," Medical physics international, 1 (2013); Ipsen et al., "Target tracking accuracy and latency with different 4D ultrasound systems-a robotic phantom study," Current Directions in Biomedical Engineering, 6(1) (2020); Queirós et al., "Fast left ventricle tracking using localized anatomical affine optical flow," International journal for numerical methods in biomedical engineering, 33(11), e2871 (2017); Roujol et al., "Characterization of respiratory and cardiac motion from electroanatomical mapping data for improved fusion of MRI to left ventricular electrograms," PloS one, 8(11), e78852 (2013); Baker et al., "Prostate displacement during transabdominal ultrasound image-guided radiotherapy assessed by real-time four-dimensional transperineal monitoring," Acta Oncologica, 54(9), 1508-1514 (2015); Khalil et al., "An Overview on Image Registration Techniques for Cardiac Diagnosis and Treatment," Cardiology research and practice, 2018 (2018); Che et al., "Ultrasound registration: A review," Methods, 115, 128-143 (2017); Hoogeman et al., "Clinical accuracy of the respiratory tumor tracking system of the cyberknife: assessment by analysis of log files," International Journal of Radiation Oncology* Biology* Physics, 74(1), 297-303 (2009); Depuydt et al., "Treating patients with real-time tumor tracking using the Vero gimbaled linac system: implementation and first review," Radiotherapy and Oncology, 112(3), 343-351 (2014); Keall et al., "The management of respiratory motion in radiation oncology report of AAPM Task Group 76a" (2006); Blanck et al., "Radiosurgery for ventricular tachycardia: preclinical and clinical evidence and study design for a German multi-center multi-platform feasibility trial (RAVENTA)," Clin Res Cardiol 109, 1319-1332 (2020); Zei, et al. "Ablative Radiotherapy as a Noninvasive Alternative to Catheter Ablation for Cardiac Arrhythmias" Curr Cardiol Rep (2017); van der Ree et al., "Cardiac Radioablation—a Systematic Review", Heart Rhythm (2020); Graeff et al., "Noninvasive cardiac arrhythmia ablation with particle beams", Med Phys 45 (11) (2018); O'Shea et al., "Review of ultrasound image guidance in external beam radiotherapy part II: intra-fraction motion management and novel applications", Physics in Medicine & Biology, v61(8) (2016); Fontanarosa et al., "Review of ultrasound image guidance in external beam radiotherapy: I. Treatment planning and inter-fraction motion management", Physics in Medicine & Biology, v60(3), R77 (2015); Bertholet et al., "Real-time intrafraction motion monitoring in external beam radiotherapy", Physics in Medicine 64 (15) (2019); Ipsen, "See what you treat: 4d ultrasound imaging for real time motion compensation in the liver", PhD Thesis University of Luebeck (2019); Ipsen et al, "Radiotherapy beyond cancer: Target localization in real-time MRI and treatment planning for cardiac radiosurgery", Med Phys 41 (12) (2014); Poon et al., "Technical Note: Cardiac synchronized volumetric modulated arc therapy for stereotactic arrhythmia radioablation—Proof of principle", Med Phys 47 (8) 2020.

Any incorporation by reference of documents herein is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A method for irradiating a target tissue, the method comprising:

affixing a multiplanar ultrasound probe to a probe holder affixed to a location on an external surface of a patient's thorax, the probe holder including a plurality of fiducial markers configured indicate position and orientation of the multiplanar ultrasound probe;

causing a localization system comprising a camera and positioned within a treatment room to generate time-wise positional data indicative of a location the plurality of fiducial markers in the treatment room, the time-wise positional data corresponding to a reference coordinate system having a fixed position in the treatment room;

causing the multiplanar ultrasound probe to generate a series of time-wise images along intersecting planes of the target tissue;

generating reference pixel coordinates based on the time-wise images and the time-wise positional data, the reference pixel coordinates corresponding to the reference coordinate system;

causing an ECG to generate time-wise cardiac phase data;

correlating, as a function of time, the time-wise images, the reference pixel coordinates, the time-wise positional data, and the time-wise cardiac phase data to generate a correlated treatment dataset;

registering the correlated treatment dataset to a previously correlated dataset to generate a registered correlated dataset; and gating irradiation of the target tissue based on one or both of the registered correlated dataset or the cardiac phase data.

2. The method of claim 1, wherein the localization system is configured to assist orienting the patient with respect to the reference coordinate system.

3. The method of claim 1, further comprising controlling irradiation of the target tissue based on one or both of a cardiac phase gating window and a respiratory gating window.

4. The method of claim 3, further comprising receiving as an input the cardiac phase gating window or the respiratory gating window.

5. The method of claim 1, wherein the correlated treatment dataset is registered to the previously correlated dataset using rigid registration.

6. The method of claim 3, wherein the respiratory gating window specifies a range of heart displacements or a portion of a respiratory cycle during which the target tissue is irradiated.

7. The method of claim 1, wherein the probe holder is configured to hold the multiplanar ultrasound probe in contact with the exterior surface of the patient's thorax.

8. The method of claim 1, wherein the previously correlated dataset is a correlated simulation dataset.

* * * * *